United States Patent
Farwick et al.

(10) Patent No.: US 11,345,936 B2
(45) Date of Patent: *May 31, 2022

(54) PRODUCTION OF FRAMBINONE BY A RECOMBINANT FUNGAL MICROORGANISM

(71) Applicant: LESAFFRE et COMPAGNIE, Paris (FR)

(72) Inventors: Alexander Matthias Farwick, Munich (DE); Thomas Desfougeres, Dissay (FR); Georges Pignede, Marcq en Baroeul (FR); Anaïs Roussel, Marquette Lez Lille (FR); Isabelle Mouly, Marcq-en-Baroeul (FR); Brieuc Morvan, Saint Simeon de Bressieux (FR)

(73) Assignee: LESAFFRE et COMPAGNIE, Paris (FR)

( * ) Notice: Subject to any disclaimer, the term of this patent is extended or adjusted under 35 U.S.C. 154(b) by 104 days.

This patent is subject to a terminal disclaimer.

(21) Appl. No.: 17/004,863

(22) Filed: Aug. 27, 2020

(65) Prior Publication Data

US 2020/0392545 A1 Dec. 17, 2020

Related U.S. Application Data

(63) Continuation of application No. 16/302,527, filed as application No. PCT/FR2017/051407 on Jun. 2, 2017, now Pat. No. 10,793,880.

(30) Foreign Application Priority Data

Jun. 3, 2016 (FR) ...................... 1655089

(51) Int. Cl.
*C12P 7/26* (2006.01)
*C07C 49/245* (2006.01)
*C12N 1/16* (2006.01)
*C12N 1/18* (2006.01)
*C12N 9/02* (2006.01)
*C12N 9/10* (2006.01)
*C12N 15/52* (2006.01)
*C12P 7/22* (2006.01)
*C12R 1/865* (2006.01)

(52) U.S. Cl.
CPC .............. *C12P 7/26* (2013.01); *C07C 49/245* (2013.01); *C12N 1/16* (2013.01); *C12N 1/185* (2021.05); *C12N 9/001* (2013.01); *C12N 9/0071* (2013.01); *C12N 9/1029* (2013.01); *C12N 15/52* (2013.01); *C12P 7/22* (2013.01); *C12R 2001/865* (2021.05); *C12Y 401/0108* (2013.01); *C12Y 403/01023* (2013.01); *C12Y 403/01024* (2013.01); *C12Y 602/01012* (2013.01)

(58) Field of Classification Search
None
See application file for complete search history.

(56) References Cited

U.S. PATENT DOCUMENTS 6,521,748 B2   2/2003   Tang

FOREIGN PATENT DOCUMENTS

| EP | 2957629 A1 | 12/2015 |
|---|---|---|
| GB | 2416769 A | 2/2006 |
| GB | 2416770 A | 2/2006 |

OTHER PUBLICATIONS

Abe et al., Benzalacetone synthase. A novel polyketide synthase that plays a crucial role in the biosynthesis of phenylbutanones in Rheum palmatum, *Eur. J. Biochem.* 268:3354-9 (2001). (2001 Abstract Only).
Bassard et al., Protein-protein and protein-membrane associations in the lignin pathway, *Plant Cell.* 24:4465-82 (2012). (2012 Abstract Only).
Beekwilder et al., Microbial production of natural raspberry ketone, *Biotechnol. J.* 2:1270-9 (2007).
Berner et al., Genes and enzymes involved in caffeic acid biosynthesis in the actinomycete Saccharothrix espanaensis, *J. Bacteriol.* 188:2666-73 (2006). (2006 Abstract Only).
Borejsza-Wysocki et al., Aromatic Polyketide Synthases (Purification, Characterization, and Antibody Development to Benzalacetone Synthase from Raspberry Fruits), *Plant Physiol.* 110:791-799 (1996). (1996 Abstract Only).
Ehlting et al., Three 4-coumarate:coenzyme A ligases in *Arabidopsis thaliana* represent two evolutionarily divergent classes in angiosperms, *Plant J.* 19:9-20 (1999). (1999 Abstract Only).
Goldstein et al., Three new dominant drug resistance cassettes for gene disruption in *Saccharomyces cerevisiae*, *Yeast.* 15:1541-53 (1999). (1999 Abstract Only).
Guldener et al., A new efficient gene disruption cassette for repeated use in budding yeast, *Nucleic Acids Res.* 24:2519-24 (1996). (1996 Abstract Only).
Guldener et al., A second set of loxP marker cassettes for Cre-mediated multiple gene knockouts in budding yeast, *Nucleic Acids Res.* 30:e23 (2002). (2002 Abstract Only).
Hazelwood et al., The Ehrlich pathway for fusel alcohol production: a century of research on *Saccharomyces cerevisiae* metabolism, *Appl. Environ. Microbiol.* 74:2259-56 (2008).

(Continued)

*Primary Examiner* — Suzanne M Noakes
*Assistant Examiner* — Jae W Lee
(74) *Attorney, Agent, or Firm* — Marshall, Gerstein & Borun LLP

(57) ABSTRACT

The invention relates to a genetically modified fungal microorganism for the production of frambinone, the microorganism having the following characteristics: —the capacity to produce frambinone from tyrosine; and —a limited capacity or no capacity to break tyrosine down into tyrosol, p-hydroxyphenylacetaldehyde and/or p-hydroxyphenylacetate; and to the use of same for producing frambinone.

Figure 1:
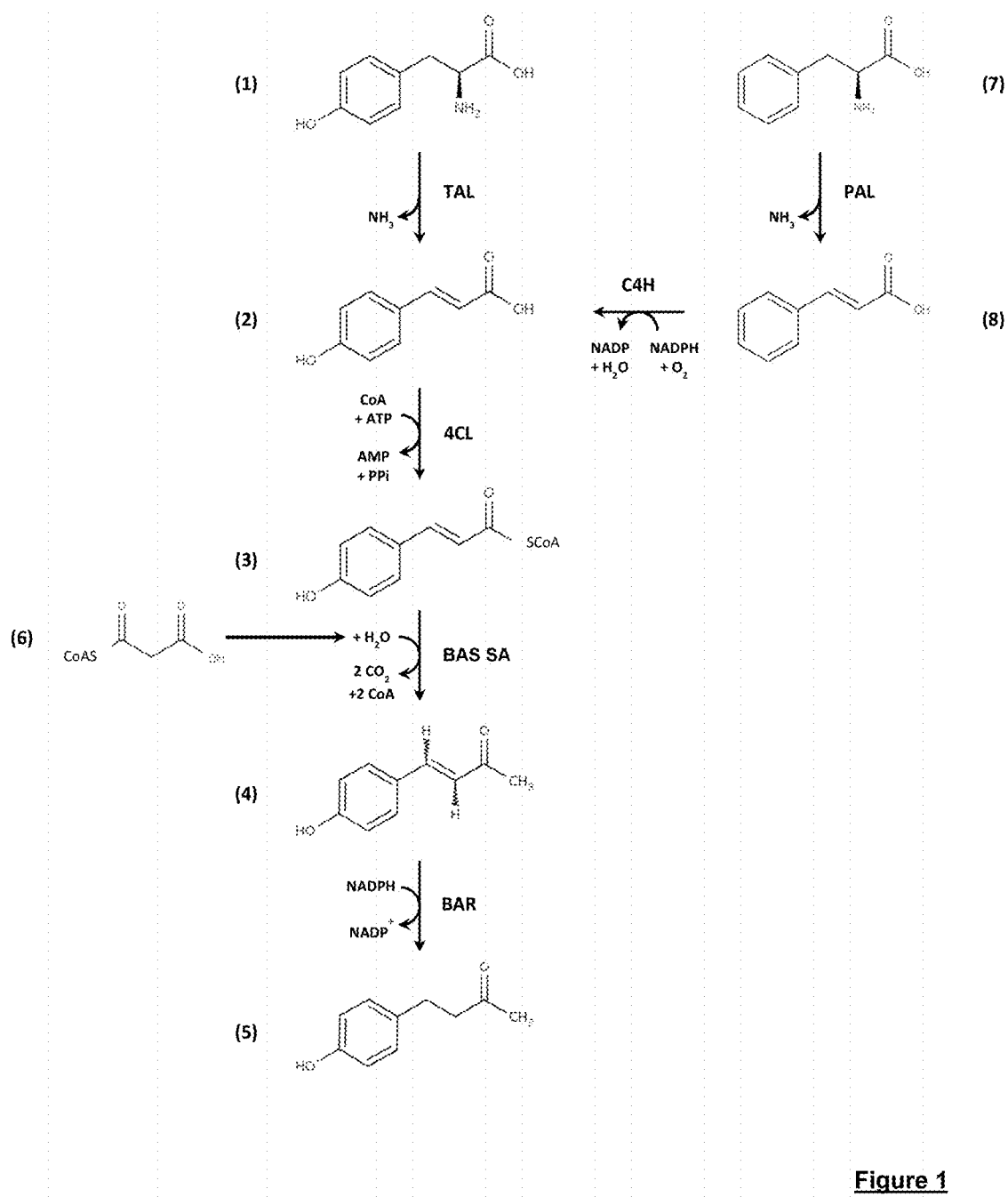

6 Claims, 4 Drawing Sheets
Specification includes a Sequence Listing.

(56) References Cited

OTHER PUBLICATIONS

International Search Report Written Opinion, PCT/FR2017/051407 (dated Sep. 11, 2017).
Janke et al., A versatile toolbox for PCR-based tagging of yeast genes: new fluorescent proteins, more markers and promoter substitution cassettes, *Yeast.* 21:947-62 (2004). (2004 Abstract Only).
Jeandet et al., Metabolic engineering of yeast and plants for the production of the biologically active hydroxystilbene, resveratrol, *J. Biomed. Biotechnol.* 1-14 (2012).
Klesk et al., Aroma extract dilution analysis of cv. Meeker (*Rubus idaeus* L.) red raspberries from Oregon and Washington, *J Agric. Food Chem.* 52:5155-61 (2004). (2004 Abstract Only).
Kneen et al., Characterization of a thiamin diphosphate-dependent phenylpyruvate decarboxylase from *Saccharomyces cerevisiae, FEBS. J.* 278:1842-53 (2011). (2011 Abstract Only).
Knobloch et al., 4-Coumarate:CoA ligase from cell suspension cultures of Petroselinum hortense Hoffm. Partial purification, substrate specificity, and further properties, *Arch. Biochem. Biophys.* 184:237-48 (1977). (1977 Abstract Only).
Koeduka et al., Characterization of raspberry ketone/zingerone synthase, catalyzing the alpha, beta-hydrogenation of phenylbutenones in raspberry fruits, *Biochem. Biophys. Res. Commun.* 412:104-8 (2011). (2011 Abstract Only).
Kyndt et al., Characterization of a bacterial tyrosine ammonia lyase, a biosynthetic enzyme for the photoactive yellow protein, *FEBS Lett.* 512:240-4 (2002). (2002 Abstract Only).
Larsen et al., Relations between the Content of Aroma Compounds and the Sensory Evaluation of 10 Raspberry Varieties (*Rubus idaeus* L), *Acta. Agric. Scand.* 41:447-454 (1991). (1991 Abstract Only).
Lee et al., Heterologous production of raspberry ketone in the wine yeast *Saccharomyces cerevisiae* via pathway engineering and synthetic enzyme fusion, *Microb. Cell Fact.* 15:49 (2016).
Lee et al., Two divergent members of a tobacco 4-coumarate:coenzyme A ligase (4CL) gene family. cDNA structure, gene inheritance and expression, and properties of recombinant proteins, *Plant Physiol.* 112:193-205 (1996). (1996 Abstract Only).
Lussier et al., Engineering microbes for plant polyketide biosynthesis, *Comput. Struct. Biotechnol. J.* 1-11 (2012).
Morita et al., A structure-based mechanism for benzalacetone synthase from Rheum palmatum, *Proc. Natl. Acad. Sci. USA.* 107:669-73 (2010). (2010 Abstract Only).
Qiao et al., Engineering lipid overproduction in the oleaginous yeast *Yarrowia lipolytica, Metab. Eng.* 29:56-65 (2015). (2015 Abstract Only).
Rodriguez et al., Establishment of a yeast platform strain for production of p-coumaric acid through metabolic engineering of aromatic amino acid biosynthesis, *Metab. Eng.* 31:181-8 (2015).
Rosler et al., Maize phenylalanine ammonia-lyase has tyrosine ammonia-lyase activity, *Plant Physiol.* 113:175-9 (1997).
Sauer, Functional expression of the cre-lox site-specific recombination system in the yeast *Saccharomyces cerevisiae, Mol. Cell. Biol.* 7:2087-96 (1987). (1987 Abstract Only).
Schuckel et al., A gene-fusion approach to enabling plant cytochromes p450 for biocatalysis, *Chembiochem.* 13:2758-63 (2012). (2012 Abstract Only).
Shin et al., Production of resveratrol from tyrosine in metabolically engineered *Saccharomyces cerevisiae, Enzyme Microb. Technol.* 51:211-6 (2012). (2012 Abstract Only).
Steensma et al., Plasmids with the Cre-recombinase and the dominant nat marker, suitable for use in prototrophic strains of *Saccharomyces cerevisiae* and Kluyveromyces lactis, *Yeast.* 18:469-72 (2001). (2001 Abstract Only).
Vuralhan et al., Identification and characterization of phenylpyruvate decarboxylase genes in *Saccharomyces cerevisiae, Appl. Environ. Microbiol.* 69:4534-41 (2003). (2003 Abstract Only).
Vuralhan et al., Physiological characterization of the ARO10-dependent, broad-substrate-specificity 2-oxo acid decarboxylase activity of *Saccharomyces cerevisiae, Appl. Environ. Microbiol.* 71:3276-84 (2005). (2005 Abstract Only).
Winkel, Metabolic channeling in plants, *Annu. Rev. Plant. Biol.* 55:85-107 (2004). (2004 Abstract Only).

PRODUCTION OF FRAMBINONE BY A RECOMBINANT FUNGAL MICROORGANISM

CROSS-REFERENCE TO RELATED APPLICATIONS AND INCORPORATION BY REFERENCE

This application is a continuation of U.S. patent application Ser. No. 16/302,527, filed Nov. 16, 2018, which is a U.S. national phase pursuant to 35 U.S.C. § 371 of International Patent Application No. PCT/FR2017/051407, filed Jun. 2, 2017, which claims priority to French Application No. 1655089, filed Jun. 3, 2016, the disclosures of which are all herein incorporated by reference in their entireties.

This application contains, as a separate part of disclosure, a Sequence Listing in computer-readable form (filename: 53662A_Seqlisting.txt; Size: 43,436 bytes; Created: Aug. 27, 2020), which is incorporated by reference in its entirety.

FIELD OF THE INVENTION

The present invention relates to methods for effectively producing frambinone from tyrosine using fungal microorganisms and suitable culture conditions.

DESCRIPTION OF THE PRIOR ART

Raspberry flavor (*Rubus idaeus*) is linked to more than 200 compounds, but frambinone, a natural phenolic compound, is the compound with the greatest impact, defining its characteristic taste (Klesk et al., 2004, J. Agric. Food Chem. 52, 5155-61; Larsen et al., 1991, Acta Agric. Scand. 41, 447-54). It can also be found in other fruits and vegetables, including peaches, apples and rhubarb (Beekwilder et al., 2007, Biotechnol. J. 2, 1270-79). As it is present only in small amounts in raspberries (1-4 mg per kg of fruit), natural frambinone is highly valuable (Larsen et al., 1991). Because it has limited natural availability, producing it by means of biotechnology is highly desirable.

Frambinone (CAS no: 5471-51-2), also called raspberry ketone or 4-(4-hydroxyphenyl)butane-2-one, has the following structure:

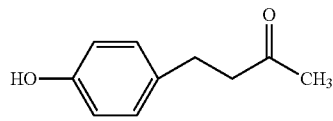

Frambinone can be used in many applications, notably in the food business and for cosmetics (as fragrance), for agriculture (as bait/trap for insects), in the health industry (as a weight-loss product) or in medicine (as a melanogenisis inhibitor).

Frambinone can be obtained from a 4-step biosynthesis, starting with aromatic amino acid L-tyrosine as substrate (FIG. 1: Beekwilder et al., 2007, Biotechnol. J. 2, 1270-79): Tyrosine is deaminated by a tyrosine ammonia-lyase TAL, EC 4.3.1.23) to form coumaric acid. Catalyzed by a 4-coumerate:CoA ligase (4CL, EC 6.2.1.12), a Coenzyme A (CoA) molecule is grafted onto coumaric acid. The coumaroyl-CoA is then converted by a benzalacetone synthase (BAS, EC 2.3.1.212) into 4-hydroxybenzalacetone. This reaction is a decarboxylating condensation and uses a malonyl-CoA unit as co-substrate. The final step is reduction of the 4-hydroxybenzalacetone to frambinone by a benzalacetone reductase (BAR EC 1.3.1.x).

An alternative substrate for the production of frambinone is coumaric acid, an intermediate in the path described above (denoted (2) in FIG. 1) However, in light of the price of the substrates used for bioconversion, industrial applications are only profitable when tyrosine is used rather than coumaric acid.

L-phenylalanine (denoted (7) in FIG. 1) can also be used as a substrate as it can be converted into coumaric acid via cinnamic acid (denoted (8) in FIG. 1) In fact, formation of frambinone in plants uses a general phenylpropanoids path, which starts with phenylalanine (Borejsza-Wysocki and Hrazdina, 1994, Phytochemistry 35, 623-28.). The first step is deamination catalyzed by a phenylalanine ammonia lyase (PAL. EC 4.3.1.24) The cinnamic acid produced is then hydroxylated by cinnamate 4-hydroxylase (C4H, EC 1.14.13.11) to form coumaric acid, which is converted as described above. C4H is a P450 cytochrome and is linked to the endoplasmic reticulum membrane. Its expression seems problematic and full activity also requires an additional enzyme (cytochrome P450 reductase, CPR) (Bassard et al., 2012, Plant Cell 24, 4465-82; Schückel et al., 2012, ChemBioChem 13, 2758-63; Winkel, 2004, Rev. Plant Biol. 55, 85-107).

Biosynthesis of two other compounds of biotechnological interest, resveratrol and naringenin, show many similarities to the path proposed for frambinone (Jeandet et al., 2012, J. Biomed. Biotechnol. 2012, 1-14; Lussier et al., 2012, Comput. Struct. Biotechnol. J. 3, 1-11.). TAL and 4CL are used to convert tyrosine and coumaric acid into coumaroyl-CoA. A stilbene synthase (STS) or chalcone synthase (CHS) then catalyzes the consecutive condensation with three malonyl-CoA units to form resveratrol or chalcone naringenin, respectively.

In light of the interest in an alternative production to the chemical synthesis of frambinone, transposing these ways of synthesizing recombinant microorganisms has been attempted, in particular in *Escherichia coli* and *Saccharomyces cerevisiae*.

GB 2 416 769 in particular describes the possibility of producing frambinone using a microorganism (particularly bacteria and yeast) containing a 4CL coding sequence and BAS, at least one from heterologous source. It can additionally include a BAR, C4H, PAL and/or CHS coding sequence, the BAR coding sequence being advantageously endogenic. In the examples, this document reports:

cloning the raspberry gene CHS;
cloning the tobacco gene 4CL;
cloning the rhubarb gene BAS;
the transformation of *E. coli* with the raspberry gene BAR;
the production of benzalacetone and frambinone (0.2 µg in 50 mL) from coumaric acid in *E. coli* transformed with BAS and 4CL;
the production of frambinone from benzalacetone in *E. coli* having endogenous BAR activity.

Based on the assumption that CHS has BAS activity, GB 2 416 770 describes the possibility of producing benzalacetone and frambinone with a microorganism comprising a 4CL coding sequence (tobacco, for example) and CHS (raspberry bush or *petunia*), at least one being a heterologous source. It can additionally include a BAR coding sequence (raspberries for example), C4H and PAL. In the examples, this document reports:

the production of benzalacetone and naringenin from coumaric acid in *E. coli* transformed with CHS and 4CL;

the building of a mutated protein CHS (CHS*) presumed to have higher BAS activity.

the production of benzalacetone and frambinone (14.2/0.3 µg in 50 mL) from coumaric acid in *E. coli* with endogenous BAR activity and transformed with CHS/ CHS* and 4CL;

the production of benzalacetone from coumaric acid in *S. cerevisiae* (with endogenous BAR activity) transformed with CHS and 4CL. No value is given in connection with frambinone. Furthermore, the mutant protein CHS* seems ineffective.

Similarly, Beekwilder et al. (2007, Biotechnol. J. 2, 1270-79) only report the successful production of frambinone from coumaric acid in *E. coli* with CHS and 4CL but with a yield of 0.3 mg/L. There has been no convincing data reported for production with yeast.

Recently, Lee et al. (2016, Microb. Cell Factories 15. doi:10.1186/s12934-016-0446-2) have demonstrated the synthesis of frambinone from coumaric acid by expressing a 4CL gene and BAS in *S. cerevisiae* (up to 8 mg/L). Furthermore, the expression of PAL/TAL and C4H made de novo production of frambinone possible (up to 4 mg/L).

Moreover, Rodriguez et al. (2015, Metabolic Engineering 31, 181-188) described a genetically modified yeast for the production of coumaric acid, the precursor of flavonoids like resveratrol and naringenin. So it is reported that inactivation of genes PDC5 and ARO10 coding a pyruvate decarboxylase and a phenylpyruvate decarboxylase, respectively, leads to overproduction of coumaric acid.

There is, then, an obvious need to develop new technical solutions offering effective production of frambinone.

DESCRIPTION OF THE INVENTION

Definitions

The definitions below correspond to the meaning generally used in the context of the invention and should be taken into account, unless another definition is explicitly indicated.

Within the meaning of the invention, the articles "a" and "an" are used to refer to one or more (for example, at least one) units of the grammatical subject of the article. As an example, "an element" refers to at least one element, i.e., one or more elements.

The terms "about" or "approximately", used in reference to a measurable value such as a quantity, a duration, and other similar values, must be understood as encompassing measurement uncertainties of ±20% or ±10%, preferably ±5%, still more preferably ±1%, and particularly preferably ±0.1% of the specified value.

Intervals: throughout the present description, the various features of the invention may be presented in the form of intervals of values. It must be understood that the description of values in the form of intervals is intended solely to make reading easier and must not be interpreted as a rigid limitation of the scope of the invention. As a result, the description of an interval of values should be considered as specifically disclosing all of the possible intermediate intervals as well as each of the values within this interval. For example, the description of an interval from 1 to 6 should be considered as specifically describing each of the intervals that it comprises, such as the intervals from 1 to 3, from 1 to 4, from 1 to 5, from 2 to 4, from 2 to 6, from 3 to 6, etc., as well as each of the values in this interval, for example 1, 2, 2.7, 3, 4, 5, 5.3 and 6. This definition is valid independently of the scope of the interval.

The term "isolated" must be understood in the context of the invention as being synonymous with withdrawn or removed from its natural environment or state. For example, an isolated nucleic acid or peptide is a nucleic acid or peptide taken out of the natural environment in which it is typically found, whether it involves a plant or a living animal, for example. Thus, a nucleic acid or a peptide naturally present in a living animal is not an isolated nucleic acid or peptide within the meaning of the present invention, while the same nucleic acid or peptide, partially or completely separated from the other elements present in its natural context, is in turn "isolated" within the meaning of the invention. An isolated nucleic acid or peptide may exist in a substantially purified form, or may exist in a non-native environment, for example a host cell.

In the context of the invention, the following abbreviations are used for the most common nucleic acid bases. "A" refers to adenosine, "C" refers to cytosine, "G" refers to guanosine, "T" refers to thymidine, and "U" refers to uridine.

Unless otherwise indicated, within the meaning of the invention, a "sequence of nucleotides coding for a sequence of amino acids" refers to all of the nucleotide sequences that code for the amino acid sequence, including the degenerated nucleotide sequences making it possible to obtain said sequence of amino acids. The nucleotide sequence that codes for a protein or an RNA or a cDNA may optionally comprise introns.

The terms "coding" or "coding for", "code" or "code for" refer to the property inherent to the specific sequences of nucleotides in a polynucleotide, such as a gene, a cDNA or a mRNA, to serve as a matrix for the synthesis of other polymers and macromolecules in biological processes, having either a defined sequence of nucleotides (for example rRNA, tRNA and mRNA), or a defined sequence of amino acids, and the biological properties resulting therefrom. Thus, a gene codes for a protein if the transcription and the translation of the mRNA corresponding to this gene produce the protein in a cell or another biological system. Both the coding strand, whose nucleotide sequence is identical to the mRNA sequence and which is generally described in the listings of sequences and databases, and the non-coding strand, used as matrix for the transcription of a gene or cDNA, can be designated as coding for the protein or another product of this gene or cDNA.

The term "polynucleotide" as used in the context of the invention is defined as a chain of nucleotides. Furthermore, the nucleic acids are nucleotide polymers. Thus, the terms nucleic acids and polynucleotides as used in the scope of the invention are interchangeable. It is well known in the field of molecular biology and genetic engineering that nucleic acids are polynucleotides, which can be hydrolyzed into monomers. Nucleotides in monomer form can be hydrolyzed into nucleosides. As used in the context of the invention, the term polynucleotide refers, non-limitingly, to any type of nucleic acid molecules, i.e., where the nucleic acid molecules can be obtained by any means available in the art, including by recombinant means, namely the cloning of sequences of nucleic acids from a recombinant library or the genome of a cell, by using ordinary cloning technologies such as PCR, or by synthesis.

Within the meaning of the invention, the terms "peptide", "polypeptide" and "protein" are used interchangeably and refer to a compound made up of amino acid residues covalently bonded by peptide bonds. By definition, a protein contains at least two amino acids, without limitation regarding the maximum number of amino acids. Polypeptides indifferently comprise several peptides and/or proteins, which in turn comprise two or more amino acids linked to one another by peptide bonds. As used here, the term refers both to short chains, which are also commonly referred to in the art as peptides, oligopeptides and oligomers, for example, and longer chains, which are generally referred to in the art as proteins, many types of which exist. "Polypeptides" for example comprise biologically active fragments, substantially homologous polypeptides, oligopeptides, homodimers, heterodimers, polypeptide variants, modified polypeptides, derivatives, analogs, fusion proteins, among others. Polypeptides comprise natural peptides, recombinant peptides, synthetic peptides, or a combination thereof.

The terms "homologous" and "identical" refer to the similarity of sequence or identity of sequence between two polypeptides or between two nucleic acid molecules. When a position in each of the two compared sequences is occupied by the same amino acid monomer base or sub-unit (for example, when a position in each of the two DNA molecules is occupied by an adenine), then the molecules are homologous or identical for this position. The percentage of identity between two sequences depends on the number of corresponding positions shared by the two sequences, and corresponds to this number divided by the number of positions compared and multiplied by 100. For example, if 6 out of 10 of the positions in two paired sequences are identical, then the two sequences are 60% identical. As a general rule, the comparison is done by aligning the two sequences so as to provide maximal homology/identity.

A "vector" within the meaning of the invention is a molecular construct that comprises an isolated nucleic acid and that can be used to deliver the isolated nucleic acid to the inside of a cell. Many vectors are known in the art, including, but not limited to, linear polynucleotides, polynucleotides associated with ionic or amphiphilic compounds, plasmids and viruses. Thus, the term "vector" for example refers to a plasmid with autonomous replication or a virus. The term must also be interpreted as comprising non-plasmid or non-viral compounds that facilitate the transfer of nucleic acids into the cells, for example compounds of polylysine, liposomes, and the like.

The term "expression vector" refers to a vector comprising a recombinant polynucleotide, which comprises expression control sequences operationally linked to a nucleotide sequence to be expressed. An expression vector in particular comprises cis-acting expression elements; other elements for the expression can be provided by the host cell or by an in vitro expression system. The expression vectors within the meaning of the invention include all those known in the art, such as cosmids, plasmids (for example naked or contained in liposomes) and viruses (for example lentiviruses, retroviruses, adenoviruses and adeno-associated viruses), which incorporate the recombinant polynucleotide.

The term "promoter" as used here is defined as a DNA sequence recognized by the synthesis machinery of the cell, or the introduced synthesis machinery, necessary to initiate the specific transcription of a sequence of polynucleotides.

Within the meaning of the invention, the terms "promoter/regulator sequence" refer to a nucleic acid sequence, necessary for the expression of the polynucleotide linked operationally to the promoter/regulator sequence. In some cases, this sequence may be the base sequence of the promoter, while in other cases, this sequence may also comprise an activator sequence and other regulator elements, useful for the expression of the polynucleotide. The promoter/regulator sequence may for example be a sequence allowing the expression of the polynucleotide that is specific to a tissue, i.e., preferably being produced in that tissue.

Within the meaning of the invention, a "constitutive" promoter is a nucleotide sequence which, when operationally linked to a polynucleotide, leads to an expression of the polynucleotide under most or all of the physiological conditions of the cell.

Within the meaning of the invention, an "inducible" promoter is a nucleotide sequence which, when operationally linked to a polynucleotide, leads to an expression of the polynucleotide only when an inducer of the promoter is present in the cell.

DETAILED DESCRIPTION OF THE INVENTION

The present invention concerns a genetically modified fungal microorganism for the production of frambinone, said microorganism having the following characteristics:
  a capacity to produce frambinone from tryosine; and
  a limited capacity or no capacity to break tyrosine down into tyrosol, p-hydroxyphenylacetaldehyde and/or p-hydroxyphenylacetate.

Within the scope of the invention, the expression "genetically modified microorganism" means that the microorganism according to the invention is not found in nature and is modified by introducing new genetic elements and/or deleting or modifying endogenous genetic elements of the microorganism. Such a microorganism can be subject to selection pressure, combining directed mutagenesis and being cultured in the selection medium.

In what follows and for reasons of simplification, the term "genetic element" is equivalent to "gene" or "sequence". A nucleic acid sequence, then, can have any type of functionality. For example, it could be a coding sequence (coding specifically for an enzyme from the synthesis or degradation pathway of interest), or a regulatory sequence, particularly a promoter or a terminator. Especially when a coding sequence is concerned, it is optimizable, that is, modifiable to integrate the preferred codons of the host, here a fungal microorganism, wherein this sequence is expressed. According to another preferred embodiment, only the coding sequence in the gene of interest, or ORF ("Open Reading Frame") is isolated and implemented.

According to an initial phase, the new genetic elements introduced in the microorganism target of the invention are genetic elements called exogenous or heterologous elements, which can also be synthetic or come from other organisms (or sources). In particular, a microorganism can express exogenous or heterologous genes if they are introduced into the aforesaid microorganism with all the elements needed to express in the host microorganism.

According to another embodiment, the endogenous genes can be modified to modulate their expression and/or their activity, for example by introducing mutations into their coding sequence to modify the genetic product or modify the regulating sequences, for example, further introducing heterologous sequences or replacing endogenous regulating sequences. Modulating the endogenous genes can result in over-expression or increased activity of the endogenous gene produced or, on the other hand, decreased expression or activity.

What is more, supernumerary or additional copies of an endogenous gene can also be introduced into the microorganism thereby increasing the level of expression and thus the activity of the product coded by the gene.

The techniques used to introduce DNA into a host (or transformation) are well known to the person skilled in the art and include permeabilization of the membranes by applying an electric field (electroporation) with heat (application of a thermal shock) or chemically, using lithium acetate, for instance.

The genetic elements introduced can be integrated into the genome of the host, notably by homologous recombination or chromosomal integration, advantageously with the use of integrative cassettes, or expressed extrachromosomically assisted by plasmids or vectors. Different types of plasmids, advantageously self-replicating, are well known by the person skilled in the art, differing notably by the origin of replication, the promoter (inducible or constitutive), the marker (for instance resistance to antibiotics or capacity to grow in a selective medium) and the number of copies per cell.

Advantageously in a fungal microorganism, genetic chromosomal integration, notably of expression cassettes bearing heterologous genes or supernumerary copies of endogenous genes, is done using the technique called "modular cassette integration technique." According to a particular embodiment, the gene(s) are integrated at the HO locus. In the event of the integration of several cassettes, they are chosen for having extremities with homologous sequences, called recombination regions (RR) permitting homologous recombination and integration in the order desired and the position desired for different cassettes. Advantageously, one of the cassettes called "cassette marker" codes a marker, for example resistance to an antibiotic or capacity to grow in a selective medium, making it possible to select or identify microorganisms in which chromosomal integration has taken place. Advantageously, an expression cassette comprises the coding part or ORF of a gene of interest, notably the enzymes involved in the biosynthetic path to frambinone from tyrosine, placed under control of regulator sequences, advantageously at least one promoter and one terminator, which can be the native regulator sequences of this gene or heterologous sequences chosen for their functionality and/or effectiveness in a host microorganism.

Inactivation of the endogenous genes can be done for instance by introducing by homologous recombination at the target gene level, a cassette, either at the regulator regions level, thus inhibiting gene expression, or the level of sequence coding resulting in inactivation of the gene produced. According to a particular embodiment, the cassette is a cassette marker, advantageously comprising a dominant gene marker controlled by a promoter and a terminator. Even more advantageously, said cassette comprises at its 5' and 3' extremities homologous regions in the 5' and 3' regions of the targeted gene, for example, corresponding to 5' in the promoter of the targeted gene and corresponding to 3' in the terminator of the targeted gene. The cassette can also contain loxP sites making it possible to excise said cassette from the genome due to the action of cre recombinase.

Within the scope of the invention, adapted markers are the genes conferring resistance to antibiotics that are then introduced into the culture medium of the genetically modified microorganism to ensure selection and maintenance of the genetic modification. Numerous markers are available to the person skilled in the art, for example:
  gene kanMX4 conferring resistance to geneticin (or G418);
  gene hphNT1 conferring resistance to hygromycin B;
  gene bsd conferring resistance to blasticidin;
  gene ble conferring resistance to phleomycin.

A good introduction and functionality of the genetic modifications desired can be verified by any technique known by the person skilled in the art, notably:
  selection thanks to the marker(s) present in the expression cassette or in the vector;
  targeting the genetic element introduced, for example by sequencing, by PCR ("Polymerase Chain Reaction") or hybridization ("Southern blot" or "Northern blot");
  targeting the product of the gene sequence, for example by immunological detection ("Western blot") or by measuring the associated activity, enzymatic activity for example.

As previously stated, the important elements to control gene expression are the promoters, placed upstream of the coding sequence whose expression is governed by the promoter. The genes can be thus expressed using inducible or constitutive promoters of variable force. According to a particular embodiment, the promoters used in the invention are constitutive promoters. These promoters can be homologous or heterologous. Within the context of the invention, the promoters commonly used by the person skilled in the art are, for example:
  the promoter of gene TDH3 of *S. cerevisiae*, for example that having sequence SEQ ID NO: 1;
  the promoter of gene PFK2 of *S. cerevisiae*, for example that having sequence SEQ ID NO: 4;
  the promoter of gene PGI1 of *S. cerevisiae*, for example that having sequence SEQ ID NO: 7;
  the promoter of gene PMA1 of *S. cerevisiae*, for example that having sequence SEQ ID NO: 10;
  the promoter of gene PYK1 of *S. cerevisiae*, for example that having sequence SEQ ID NO: 13;
  the promoter of gene TEF1 of *Ashbya gossypii*, for example that having sequence SEQ ID NO: 15 or *S. cerevisiae*

Other important elements to control gene expression are termination sequences, also called terminators, placed downstream of the coding sequence to be expressed. There again, they can be homologous terminators from the microorganism in question, or heterologous terminators, that is, artificial sequences or terminators from a source other than the host microorganism. Numerous termination sequences are available to the person skilled in the art, for example:
  the terminator of gene CYC1 of *Saccharomyces cerevisiae*, for example that having sequence SEQ ID NO: 3;
  the terminator of gene PFK2 of *S. cerevisiae*, for example that having sequence SEQ ID NO: 6;
  the terminator of gene PGI1 of *S. cerevisiae*, for example that having sequence SEQ ID NO: 9;
  the terminator of gene ZWF1 of *S. cerevisiae*, for example that having sequence SEQ ID NO: 12;
  the terminator of gene PYK1 of *S. cerevisiae*, for example that having sequence SEQ ID NO: 14;
  the terminator of gene TEF1 of *Ashbya gossypii*, for example that having sequence SEQ ID NO: 17.

In the context of the invention, the term "fungal microorganism" advantageously designates a yeast or a mushroom.

In the context of the invention, the term "fungal microorganism" means a "strain of fungal microorganism". Indeed, advantageously, the genetically modified fungal microorganism, object of the present invention, is obtained from an isolated strain and at least partially characterized.

Illustratively and in reference to yeasts, "yeast" is understood to be a commercial product obtained by implementing a method for producing a yeast strain. Thus, yeasts having different properties can be obtained from a single strain, where these differences are connected with the production method implemented.

More precisely, the invention targets a yeast strain, in other words, a strain belonging to the phyla ascomycetes or basidiomycetes. Advantageously, the strain belongs to the genus *Saccharomycetales*, even more advantageously to the families Debaryomycetaceae, Dipodascaceae, or Saccaromycetaceae. According to a preferred embodiment, the strain belongs to the genus *Yarrowia, Debaryomyces, Arsula, Scheffersomyces, Geotrichum, Pichia* or *Saccharomyces*. For example, it can be of the species *Yarrowia lipolytica, Debaryomyces hansenii* or *Saccharomyces cerevisiae*.

According to a particular embodiment, the strain used for constructing a strain according to the invention or for constructing a process according to the invention is strain called "industrial", as opposed to a strain called "laboratory". Industrial yeast strains are those producible using industrial substrates as a carbon source. As an example, said carbon source can be molasses from sugar cane or sugar beet.

According to an advantageous embodiment, the microorganism is chosen with at least one of the following characteristics:
  a capacity to at least partially produce frambinone from tryosine; and/or
  a limited capacity or no capacity to break tyrosine down into tyrosol, p-hydroxyphenylacetaldehyde and/or p-hydroxyphenylacetate.

Regarding the first characteristic, the microorganism to be genetically modified can have at least one endogenous enzymatic activity involved in the conversion of tyrosine into frambinone. According to a particular embodiment, 4-hydroxybenzalacetone can be converted into frambinone and naturally present a BAR activity, as detailed below:

The microorganism can be chosen for other characteristics of interest, notably for its biotechnological application (knowledge of the genome, tools available for genetic manipulation, etc.), its metabolism (notably respiratory and lipid favoring production of malonyl-CoA or acetyl-CoA, co-substrates for synthesis of frambinone), or conditions for its industrial use (aerobic growth, tolerance to stress and toxic compounds, etc.)

According to a particular embodiment, a microorganism of interest is chosen from the following list: *Beauveria bassiana, Candida boidinii, Galactomyces candidum (Geotrichum candidum), Kloeckera saturnus, Kodamaea ohmeri (Pichia ohmeri), Komagataella pastoris (Pichia pastoris), Mucor nederlandicus (Mucor subtilissimus), Pichia membranifaciens, Schwanniomyces etchellsii (Pichia etchellsii), Torulaspora delbrueckii (Saccharomyces fermentati), Wickerhamomyces anomalus (Hansenula anomala), Yarrowia lipolytica (Candida lipolytica), Saccharomyces cerevisiae, Debaryomyces hansenii*. Advantageously, it is *Saccharomyces cerevisiae, Yarrowia lipolytica* or *Debaryomyces hansenii*.

Fungal microorganisms of particular interest are *Yarrowia lipolytica* or *Debaryomyces hansenii*.

A microorganism according to the invention intended to produce frambinone using tryosine. Advantageously, such a microorganism has an improved capacity to produce frambinone from tyrosine, notably compared with strains already described or compared with the same microorganism that has not been genetically modified.

Frambinone is known to be produced from other substrates but tyrosine is clearly of interest from an economic point of view. In addition, it has been shown that adding tyrosine into a culture medium, advantageously a fermentation medium, was possible in terms of solubility and showed no noteworthy toxicity. In an appropriate manner and as seen in more detail in relation to the process according to the invention, the production of frambinone is done from tyrosine exogenous to the microorganism according to the invention, advantageously by addition into its culture medium. Typically, the concentration of tyrosine in the culture medium is greater than or equal to 50 mg/L, even greater than or equal to 100, 150, 200, 250, 300, 350, 400 or even 450 mg/L. In addition, it is advantageously less than or equal to 1 g/L, or even less than or equal to 950, 900, 850, 800, 750, 700, 650, 600, 550, 500 or even 450 mg/L.

According to another aspect, the invention also concerns the use of a microorganism as defined within the scope of the present application for the production of frambinone from tyrosine. Within the scope of the invention, production levels of frambinone by a microorganism never yet achieved are intended, advantageously a concentration in the culture medium of the microorganism greater than 4 mg/L, more advantageously greater than or equal to 5, 6, 7, 8, 9, 10, 11, 12, 13, 14, 15, 16, 17, 18, 19 or even 20, 25 or 30 mg/L. In these concentrations and under the conditions of the process according to the invention, frambinone remains soluble with no toxicity vis-a-vis the microorganisms according to the invention.

According to a first characteristic, a microorganism according to the invention or implemented in a process according to the invention is genetically modified to have the capacity to produce or synthesize frambinone from tyrosine, or even an improved capacity to produce or synthesize frambinone from tyrosine.

According to the invention, the microorganism can naturally have the capacity to synthesize frambinone from tyrosine and the purpose of the genetic modifications is to improve this capacity. Alternatively, the organism does not naturally have the capacity to synthesize frambinone from tyrosine, and the purpose of the genetic changes is to confer this capacity.

As stated and shown in FIG. 1, a path for synthesis of frambinone from tyrosine involves 4 enzyme activities, namely:
  a tyrosine ammonia lyase activity (EC 4.3.1.23), denoted TAL, capable of deaminating tyrosine to form coumaric acid;
  a 4-coumarate:CoA ligase activity (EC 6.2.1.12), denoted 4CL, capable of catalyzing the grafting of a coenzyme A molecule (CoA) on coumaric acid to form coumaroyl-CoA;
  a benzalacetone synthase (EC 2.3.1.212), denoted BAS, capable of converting coumaroyl-CoA into 4-hydroxybenzalacetone in the presence of malonyl-CoA as co-substrate;
  a benzalacetone reductase activity (EC 1.3.1.x), denoted BAR, to reduce the 4-hydroxybenzalacetone to frambinone.

According to an advantageous embodiment, the microorganism according to the invention is genetically modified to ensure or improve the production of frambinone from tyrosol. Advantageously the genetic changes permit at least one of the four aforementioned enzymatic activities to increase. For example:
  mutations in the genetic coding portion making it possible to obtain an enzyme having the activity sought or with improved activity, notably in terms of specificity and affinity with the substrate;

modification of the regulatory sequences to increase the level of expression of an endogenous gene encoding an enzyme with the activity sought;

contribution of supernumerary copy(ies) of an endogenous gene encoding an enzyme with the activity sought, optionally mutated to improve activity;

contribution of one or more copies of at least one heterologous gene (artificial or from another organism source) encoding an enzyme with the activity sought, placed under control of regulatory sequences adapted to produce the aforesaid enzyme.

Concerning TAL, the enzymes of the family of lyases having a predominant activity for tyrosine (tyrosine ammonia-lyase, EC 4.3.1.23) are rare. It often shows at least equal or even greater affinity for the substrate phenylalanine (phenylalanine/tyrosine ammonia-lyase, PAL/TAL, EC 4.3.1.25).

In certain cases, it may be desirable to choose a TAL enzyme with no or very little PAL activity so as to avoid the accumulation of the cinnamic acid intermediate, which can present a certain toxicity. Where the TAL enzyme chosen has well-known PAL activity, it may be advantageous to ensure that the microorganism additionally has C4H and/or CPR activity, and possibly to modify it to introduce sequences encoding the enzymatic activities useful in converting cinnamic acid to coumaric acid. Alternatively, one might mutate the TAL coding sequence to decrease the possibly associated PAL activity. In addition, an accumulation of cinnamic acid can exert negative feedback on TAL possibly necessitating a balanced expression of 4CL.

Note that enzymatic tests to evaluate TAL and PAL activities are well known to the person skilled in the art and are described in documents by Berner et al. (J. Microbiol., 2006, 188, 2666-73), Kyndt et al. (FEBS Lett., 2002 512, 240-44) and Rosier et al. (Plant Physiol., 1997, 113, 175-79).

Genes of interest that can be implemented within the scope of the invention are listed in Table 1 below:

| Name | Organism | Name of the gene/Uniprot | References |
|---|---|---|---|
| RgTAL | Rhodotorula glutinis/ Rhodosporidium toruloides | PAL P11544 SEQ ID NO: 18 | Vannelli et al., 2007, Metab. Eng. 9, 142-51. US 6,521,748 Santos et al., 2011, Metab. Eng. 13, 392-400 Wu et al., 2013, J. Biotechnol. 167, 404-11 Wu et al., 2014, PLoS ONE 9, E101492 Jiang et al., 2005, Appl. Environ. Microbiol. 71, 2962-69 |
| RsTAL | Rhodobacter sphaeroides | hutH Q3IWB0 | Watts et al., 2004, Chembiochem Eur. J. Chem. Biol. 5, 500-507 Watts et al., 2006, Chem. Biol. 13, 1317-26 Louie et al., 2006, Chem. Biol. 13, 1327-1338 Schroeder et al., 2008, Phytochem. 69, 1496-1506 Xue et al., 2007, J. Ind. Microbiol. Biotechnol. 34, 599-604 Wang and Yu, 2012, J. Biotechnol. 157, 258-260 Wang et al., 2011, Metab. Eng. 13, 455-463 Zhang et al., 2006, J. Am. Chem. Soc. 128, 13030-31 |
| RcTAL | Rhodobacter capsulatus | | Xue et al., 2007, J. Ind. Microbiol. Biotechnol. 34, 599-604 Kyndt et al., 2002, FEBS Lett. 512, 240-44 |
| SeTAL | Saccharothrix espanaensis | sam8 Q2EYY5 | Berner et al., 2006, J. Bacteriol. 188, 2666-73. Choi et al., 2011, J. Ind. Microbiol. Biotechnol. 38, 1657-65 Kang et al., 2012, Microb Cell Fact 11, 153 |
| CpTAL | Chitinophaga pinensis | Cpin_1853/ FlxA C7PAX7 | Schöner et al., 2014, Microb. Biotechnol. 7, 232-41 |
| TcTAL | Trichosporon cutaneum | | Vannelli et al., 2007, Enzyme Microb. Technol. 41, 413-22 |

According to a particular embodiment, the TAL protein encoded by the gene introduced in the microorganism according to the invention has the sequence SEQ ID NO: 18, or a protein sequence with at least 70%, or even 80, 85, 90, 95 or even 99% homology or sequence identity SEQ ID NO: 18 and possessing TAL activity.

According to another particular embodiment, the TAL protein coding sequence introduced into the microorganism according to the invention has the sequence SEQ ID NO: 5, or a sequence with at least 60%, even 70, 80, 85, 90, 95 or even 99% sequence identity SEQ ID NO: 5. Its expression may be placed under the control of regulatory sequences SEQ ID NO.: 4 or SEQ ID NO: 6.

Concerning 4CL, it is a priori an enzyme that is not present in the fungal microorganisms considered in the present invention. Thus and advantageously, at least one copy of at least one heterologous gene is introduced.

Note that enzymatic tests to evaluate 4CL activities are well known to the person skilled in the art and are described in documents by Ehlting et al. (Plant J., 1999, 19, 9-20), Knobloch and Hahlbrock (Arch. Biochem. Biophys., 1977, 184, 237-48) and Lee and Douglas (Plant Physiol., 1996, 112, 193-205).

The majority of the 4-coumarate:CoA ligases (4CL; EC6.2.1.12) are found in plants. Genes of interest that can be implemented within the invention are listed in Table 2 below:

| Name | Organism | Name of the gene/Uniprot | References |
|---|---|---|---|
| At4CL-1 | Arabidopsis thaliana | 4CL1 Q42524 (NCBI: AAA82888.1) SEQ ID NO: 19 | Ehlting et al., 1999, Plant J. 19, 9-20 Hamberger and Hahlbrock, 2004, Proc. Natl. Acad. Sci. U.S.A. 101, 2209-14 Watts et al., 2004, Chembiochem Eur. J. Chem. Biol. 5, 500-507 Watts et al., 2006, BMC Biotechnol. 6, 22 Koopman et al., 2012, Microb Cell Fact 11, 155 Sydor et al., 2010, Appl. Environ. Microbiol. 76, 3361-63 |

-continued

| Name | Organism | Name of the gene/Uniprot | References |
|---|---|---|---|
| Nt4CL-2 | Nicotiana tabacum | 4CL2 O24146 (NCBI: U50846) | Beekwilder et al., 2007, Biotechnol. J. 2, 1270-79. Beekwilder et al., 2006, Appl. Environ. Microbiol. 72, 5670-72 |
| Pc4CL-2 | Petroselinum crispum | 4CL2 P14913 (GenBank: CAA31697.1) | Leonard et al., 2008, Mol. Pharm. 5, 257-65 Lim et al., 2011, Appl. Environ. Microbiol. 77, 3451-60 Wu et al., 2014, PLoS ONE 9, E101492 Xu et al., 2011, Metab. Eng. 13, 578-87. Leonard et al., 2005, Appl. Environ. Microbiol. 71, 8241-48. Yan et al., 2005, Appl. Environ. Microbiol. 71, 5610-13 |
|  | Lithospermum erythrorhizon | Q42880 | Yazaki et al., 1997, Biosci. Biotechnol. Biochem. 61, 1995-2003 |
|  | Populus trichocarpa x P. deltoides |  |  |
|  | Glycine max |  |  |
| ScCCL | Streptomyces coelicolor | SCO4383 Q9K3W1 | Kaneko et al., 2003, J. Bacteriol. 185, 20-27 Miyahisa et al., 2005, Appl. Microbiol. Biotechnol. 68, 498-504 |
| Cp4CL | Chitinophaga pinensis | Cpin_1877/FlxY C7PB01 | Schöner et al., 2014, Microb. Biotechnol. 7, 232-41 |

According to a particular embodiment, the 4CL protein encoded by the gene introduced in the microorganism according to the invention has the sequence SEQ ID NO: 19, or a protein sequence with at least 70%, or even 80, 85, 90, 95 or even 99% homology or identity with sequence SEQ ID NO: 19 and possessing 4CL activity.

According to another particular embodiment, the 4CL protein coding sequence introduced into the microorganism according to the invention has the sequence SEQ ID NO: 8, or a sequence with at least 60%, even 70, 80, 85, 90, 95 or even 99% sequence identity SEQ ID NO: 8. Its expression may be placed under the control of regulatory sequences SEQ ID NO.: 7 and/or SEQ ID NO: 9.

It should be noted that the accumulation of coumaryl-CoA generated under 4CL action can engender the undesirable formation of phloretic acid and inhibit TAL activity. It is therefore important that the microorganism according to the invention has appropriate BAS activity (catalyzing the next step in synthesizing frambinone).

Concerning BAS, it is a priori an enzyme that is not present in the fungal microorganisms considered in the present invention. Thus and advantageously, at least one copy of at least one heterologous gene is introduced.

Note that enzymatic tests to evaluate BAS activities are well known to the person skilled in the art and are described in documents by Abe et al. (Eur. J. Biochem., 2001, 268, 3354-59 and Morita et al., 2010). Morita et al. (Acad. Sci. 2010, 107, 669-673).

Benzalacetone synthases (BAS; EC2.3.1.212) are part of the PKS (PolyKetone synthase) family that also includes chalcone synthases (CHS; involved for example in the synthesis of naringenin) and stilbene synthases (STS; involved for example in the synthesis of resveratrol). These enzymes accept coumaroyl-CoA and other substrates and catalyze a condensation with malonyl-CoA. Malonyl-CoA is an intermediate in the synthesis of fatty acids and its formation requires ATP. While CHS and STS add three malonyl-CoA units, BAS adds only one. However, the BAS enzymes described also have CHS activity. Genes of interest that can be implemented within the invention are listed in Table 3 below:

| Name | Organism | Name of the gene/Uniprot | References |
|---|---|---|---|
| RpBAS | Rheum palmatum | BAS SA Q94FV7 SEQ ID NO: 20 | Abe et al., 2001, Eur. J. Biochem. 268, 3354-59. Shimokawa et al., 2012, Front. Plant Sci. 3. Abe et al., 2003, J. Biol. Chem. 278, 25218-26. Abe et al., 2007, Bioorg. Med. Chem. Lett. 17, 3161-66. Jez et al., 2001, J. Ind. Microbiol. Biotechnol. 27, 393-398. Morita et al., 2010, Proc. Natl. Acad. Sci. 107, 669-673. |
| RiPKS4 | Rubus idaeus | PKS4 B0LDU5 | Kumar and Ellis, 2003, Phytochemistry 62, 513-26. Zheng and Hrazdina, 2008, Arch. Biochem. Biophys. 470, 139-145. Zheng et al., 2001, Plant Mol. Biol. 46, 1-15 Beekwilder et al., 2007, Biotechnol. J. 2, 1270-79. |
| PKS1 | Wachendorfia thyrsiflora |  | Brand et al., 2006, Planta 224, 413-28. |
| PKS1 | Polygonum cuspidatum |  | My et al., 2009, Planta 229, 1077-86 |
| PKS2 | Polygonum cuspidatum |  | Ma et al., 2009, Planta 229, 457-69. |

According to a particular embodiment, the protein BAS encoded by the gene introduced into the microorganism according to the invention has the sequence SEQ ID NO: 20, or a protein sequence with at least 70%, or even 80, 85, 90, 95 or even 99% homology or identity with sequence SEQ ID NO: 20 and possessing BAS activity.

According to another particular embodiment, the BAS protein coding sequence introduced into the microorganism according to the invention has the sequence SEQ ID NO: 11, or a sequence with at least 60%, even 70, 80, 85, 90, 95 or even 99% identity with sequence SEQ ID NO: 11. Its expression may be placed under the control of regulatory sequences, particularly a sequence promoter for SEQ ID NO.: 10 or SEQ ID NO: 13 and/or sequence terminator SEQ ID NO: 12 or SEQ ID NO: 14.

According to another particular embodiment, at least two BAS coding sequences, for example two copies of the same sequence, are introduced into the microorganism according to the invention. It should be noted that they can be placed under the control of various regulatory sequences.

The last step in synthesizing frambinone is the reduction of the α,β-double bond in p-hydroxybenzalacetone, which requires NADPH, catalyzed by benzalacetone reductase (BAR; EC 1.3.1.x). Only two enzymes with this activity have been identified to date. However, certain microorganisms have been reported to have endogenous BAR activity, E. coli and S. cerevisiae for example (Beekwilder et al., 2007, Biotechnol. J. 2, 1270-79). The first enzyme is described in document GB 2 416 769: a protein of 309 amino acids was isolated from raspberry protein fractions with BAR activity. It is homologous with isoflavone reductases (EC 1.3.1.45) and is capable of converting p-hydroxybenzalacetone into frambinone in in vitro tests carried out with purified enzyme. In 2011, Koeduka et al. (Biochem. Biophys. Res. Common. 412, 104-108) have identified a ketone/zingerone synthase of R. idaeus with BAR activity (RiRZS1, Uniprot G1FCG0). The purified protein effectively converts p-hydroxybenzalacetone into frambinone in an enzymatic test.

Note that enzymatic tests to evaluate BAR activity are well known to the person skilled in the art and are described in Koeduka et al. document (Biochem. Biophys. Res. Commun., 2011, 412, 104-108).

According to a particular embodiment, the protein BAR is encoded by a gene introduced into the microorganism according to the invention and with the sequence SEQ ID NO: 21, or a protein sequence with at least 70%, or even 80, 85, 90, 95 or even 99% homology or sequence identity SEQ ID NO: 21 and possessing BAR activity.

According to another particular embodiment, the BAR protein coding sequence is introduced into the microorganism according to the invention has the sequence SEQ ID NO: 2, or a sequence with at least 60%, even 70, 80, 85, 90, 95 or even 99% identity with sequence SEQ ID NO: 2. Its expression may be placed under the control of regulatory sequences, particularly sequences SEQ ID NO.: 1 and/or SEQ ID NO: 3.

According to a particular embodiment, the fungal microorganism according to the invention is naturally devoid of at least one enzymatic activity among 4CL and BAS, or even the 2.

Advantageously, the fungal microorganism according to the invention includes at least one heterologous sequence encoding the enzyme 4-coumarate:CoA ligase (4CL) or benzalacetone synthase (BAS), advantageously enzymes 4CL and BAS.

According to a preferred embodiment, said sequence codes a 4CL enzyme having the sequence SEQ ID NO: 19, or a protein sequence with at least 70%, or even 80, 85, 90, 95 or even 99% homology or identity with sequence SEQ ID NO: 19 and possessing 4CL activity. Preferably, this sequence comprises the sequence SEQ ID NO: 8, or a sequence with at least 60%, even 70, 80, 85, 90, 95 or even 99% sequence identity SEQ ID NO: 8. It can also comprise the sequence SEQ ID NO: 7, advantageously located upstream of the 4CL coding sequence, and/or the sequence SEQ ID NO: 9, advantageously located downstream of the 4CL coding sequence.

According to another preferred embodiment, said sequence encodes a BAS enzyme showing the sequence SEQ ID NO: 20, or a protein sequence with at least 70%, or even 80, 85, 90, 95 or even 99% homology or identity with sequence SEQ ID NO: 20 and possessing BAS activity. Preferably, said sequence includes sequence SEQ ID NO: 11 or a sequence with at least 60%, even 70, 80, 85, 90, 95 or even 99% sequence identity SEQ ID NO: 11. It can also comprise the sequence SEQ ID NO: 10 or SEQ ID NO: 13, advantageously located upstream of the BAS coding sequence, and/or the sequence SEQ ID NO: 12 or SEQ ID NO: 14, advantageously located downstream of the BAS coding sequence.

According to a particular embodiment, the fungal microorganism according to the invention comprises at least two heterologous sequences encoding the enzyme benzalacetone synthase (BAS), advantageously from the same source, even more advantageously of the same coding sequence but possibly placed under the control of different regulatory sequences.

According to another embodiment, the fungal microorganisms within the present invention do not present at least one of the following activities: TAL, 4CL, BAS and/or BAR.

Advantageously, the fungal microorganism according to the invention comprises at least one heterologous or supernumerary sequence encoding the enzyme tyrosine ammonia lyase (TAL) or benzalacetone reductase (BAR), advantageously enzymes TAL and BAR.

According to a preferred embodiment, said sequence encodes a TAL enzyme with the sequence SEQ ID NO: 18, or a protein sequence with at least 70%, or even 80, 85, 90, 95 or even 99% homology or sequence identity SEQ ID NO: 18 and possessing TAL activity. Preferably, this sequence comprises the sequence SEQ ID NO: 5, or a sequence with at least 60%, even 70, 80, 85, 90, 95 or even 99% sequence identity SEQ ID NO: 5. It can also comprise the sequence SEQ ID NO: 4, advantageously located upstream of the TAL coding sequence, and/or the sequence SEQ ID NO: 6, advantageously located downstream of the TAL coding sequence.

According to a preferred embodiment, said sequence encodes a BAR enzyme with the sequence SEQ ID NO: 21, or a protein sequence with at least 70%, or even 80, 85, 90, 95 or even 99% homology or sequence identity SEQ ID NO: 21 and possessing BAR activity. Preferably, this sequence comprises the sequence SEQ ID NO: 2, or a sequence with at least 60%, even 70, 80, 85, 90, 95 or even 99% identity with sequence SEQ ID NO: 2. It can also comprise the sequence SEQ ID NO: 1, advantageously located upstream of the BAR coding sequence, and/or the sequence SEQ ID NO: 3, advantageously located downstream of the BAR coding sequence.

According to a particular embodiment, the fungal microorganisms referred to by the present invention include at least one heterologous sequence encoding the enzymes 4-coumarate:CoA ligase (4CL) and benzalacetone synthase (BAS), and at least one heterologous or supernumerary sequence encoding the enzyme tyrosine ammonia-lyase (TAL) and benzalacetone reductase (BAR).

A particular strain of Saccharomyces cerevisiae with these characteristics, and thus a path to converting tyrosine into functional frambinone and appropriate for the target applications, is the industrial strain RK4, registered with the CNCM (National Collection of Microorganism Cultures, Pasteur Institute, 25 rue du Docteur Roux, 75724 Paris Cedex 15) dated Jun. 1, 2016 under number I-5101. This was obtained by chromosomal integration, at the level of HO locus of the strain registered with the CNCM dated Sep. 4, 2008 under number I-4071, expression cassettes encoding these 4 enzymes, as described below (See examples).

Another particular strain of Saccharomyces cerevisiae with these same characteristics is the industrial strain RK5, registered with the CNCM on Apr. 26, 2017 under number I-5199. This was obtained from strain RK4, by excising the kanMX 4 gene into the expression cassette (see examples below).

With respect to the path of synthesizing frambinone, the fungal microorganisms according to the invention may undergo other genetic modifications, such as for example:
  any means to establish or increase the capacity of the organism to synthesize the frambinone from phenylalanine, for example, via the introduction of a gene encoding a PAL enzyme. As stated, PAL enzymes are related to the TAL enzymes described above. Optionally, a TAL enzyme also showing PAL activity may be used.

any means to establish or increase the capacity of the organism to convert cinnamic acid to acid coumaric, for example via the introduction of a gene encoding a C4H enzyme, for example, optionally in combination with a gene encoding a CPR enzyme.

any means to improve the capacity of the organism to produce malonyl-CoA, for example as reported in *Y. lipolytica* (Qiao et al., 2015, Metab. Eng. 29: 56-65) or to overproduce Acetyl-Cohas carboxylase ACC1 in *S. cerevisiae* (Shin et al., 2012, Enzyme Microb. Technol. 51, 211-216).

Thus and according to a particular embodiment, the microorganism used according to the invention comprises at least one heterologous or supernumerary sequence encoding the enzyme phenylalanine ammonia lyase (TAL) or 4-(C4H), advantageously TAL and C4H enzymes.

Figure 2:
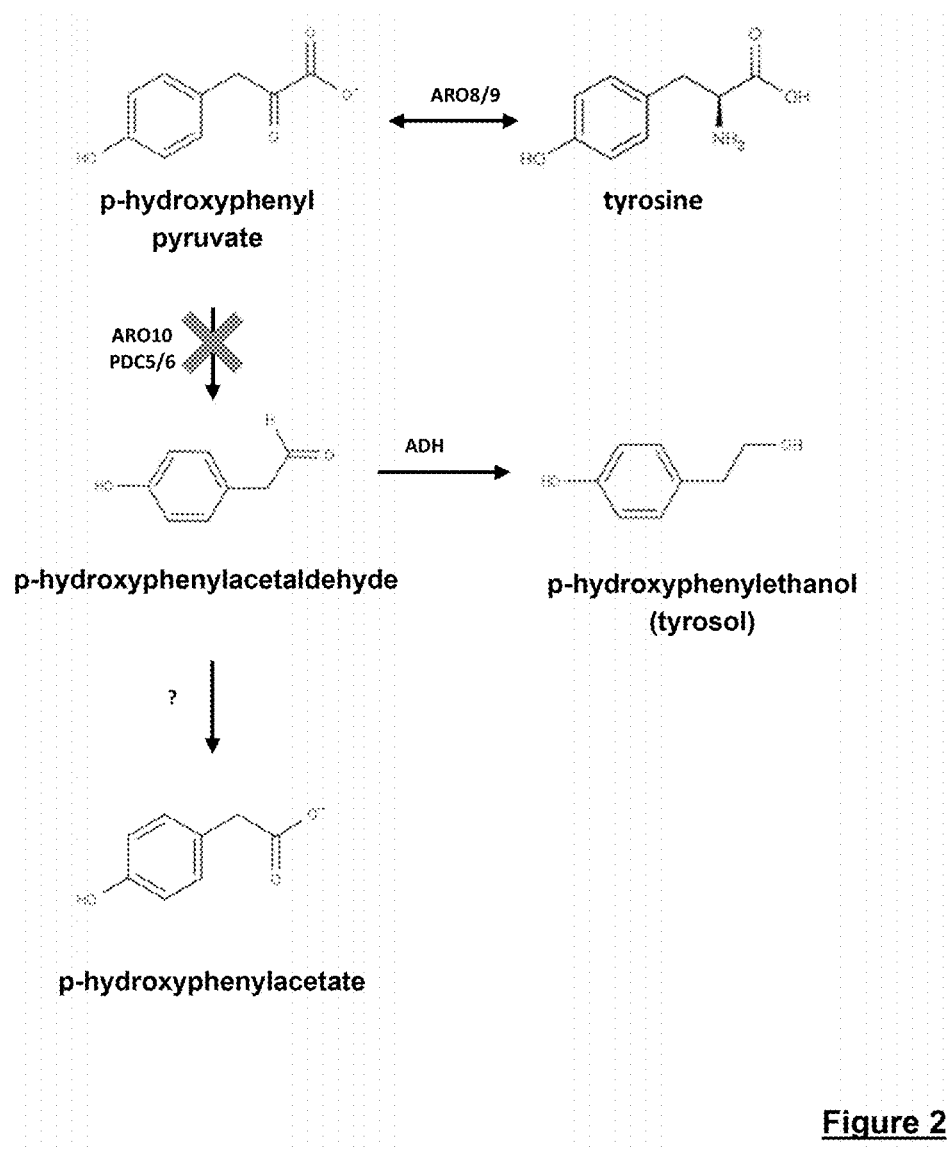

According to a second advantageous characteristic, one target fungal microorganism of the invention is earmarked in its path to break down tyrosine as illustrated in FIG. 2. According to this path, called "path of breaking tyrosine down into tyrosol", tyrosine is converted to p-hydroxyphenylacetaldehyde, which can continue in that state or be converted either into tyrosol or into p-hydroxyphenylacetate. Thus and advantageously, a target fungal microorganism within the invention has a limited capacity or no capacity to break down or to convert tyrosine into tyrosol, p-hydroxyphenylacetaldehyde and/or p-hydroxyphenylacetate.

It is evident, in the scope of the present application, that the predominant path to breaking down tyrosine into the fungal microorganisms of interest was the path for breaking tyrosine down into tyrosol, as shown in FIG. 2.

Said capacity can be evaluated as described in the section "Examples of Implementation" below, cultivating of fungal microorganisms potentially of interest in the production of frambinone, genetically modified or not, in the presence of tyrosine and following the production of tyrosol, for example by HPLC. Typically, a microorganism may prove to be of interest if in the conditions described in the experimental part, namely in conditions of aerobic fermentation conducted in the medium, advantageously an inorganic medium, for example composed of 1.7 g/L of YNB (Difco™), 5 g/L of ammonium sulfate, 2.7 g/L potassium phosphate and 20 g/L of dextrose, and containing tyrosine, advantageously at a level of 300 mg/L, the quantity of tyrosol produced is less than or equal to 150 mg/L, advantageously less than or equal to 100 mg/L, even 50, 40, 30, 20 mg/L or even 10 mg/L.

Alternatively and as is clear from FIG. 2, strains of the fungal microorganisms of interest can be selected on the basis of their hydroxyphenyl pyruvate decarboxylase (HPPDC) activity, a method of measurement described in the examples of implementation, below.

Advantageously, the HPPDC activity in the microorganism according to the invention is less than or equal to $2 \times 10^{-6}$ KAT per g of protein, advantageously less than or equal to $1 \times 10^{-6}$ KAT per g of protein, or even to $5 \times 10^{-7}$ KAT per g of protein. In the scope of the invention, it refers to the proteins extracted from the microorganism.

More specifically, the HPPDC activity measured in a microorganism according to the invention is preferentially less than or equal to $10^{-5}$ KAT per g of protein, advantageously less than or equal to $5 \times 10^{-6}$, $4 \times 10^{-6}$, $3 \times 10^{-6}$, $2 \times 10^{-6}$, $1 \times 10^{-6}$ KAT per g of protein, or even less than or equal to $9 \times 10^{-7}$, $8 \times 10^{-7}$, $7 \times 10^{-7}$, $6 \times 10^{-7}$, $5 \times 10^{-7}$ KAT per g of protein. According to a particular embodiment, it is less than or equal to $4 \times 10^{-7}$ KAT per g of protein, advantageously less than or equal to $3 \times 10^{-7}$ KAT per g of protein, even more advantageously less than or equal to $2 \times 10^{-7}$, $1.5 \times 10^{-7}$, $1 \times 10^{-7}$, or even $0.5 \times 10^{-7}$ KAT per g of protein.

Thus and according to the invention, the microorganism is selected for its low or nil capacity to break down tyrosine, assessed according to one of the two methods mentioned above. As already said, this selection of adapted microorganisms can be performed before or after the genetic modification of the said microorganism.

According to a first embodiment, the microorganism is selected for its naturally limited capacity or incapacity to break tyrosine down into tyrosol, p-hydroxyphenylacetaldehyde and/or p-hydroxyphenylacetate.

Alternatively, a microorganism of interest, in particular for its capacity to synthesize frambinone, is subjected to genetic modifications to reduce or even eliminate its capacity to break tyrosine down into tyrosol, p-hydroxyphenylacetaldehyde and/or p-hydroxyphenylacetate.

As shown in FIG. 2, this can be achieved by inhibiting or by inactivating one of the steps that ensures the transformation of tyrosine to tyrosol, p-hydroxyphenylacetaldehyde and/or p-hydroxyphenylacetate, particularly the step of deamination, decarboxylation, or even reduction.

As already stated, different means are available to the person skilled in the art to achieve this inhibition or inactivation by genetic modification of the microorganism, including the chromosomal insertion of genetic elements either exogenous at the level of the regulatory regions in such a way as to interfere with the expression of the target gene, either at the level of the coding sequence in a manner to prevent the production of the product of the gene or to lead to the production of a truncated and/or inactive protein. It is also possible to mutate the target gene at the level of critical sequences for its expression or its activity.

According to a particular embodiment, the target gene is inactivated using a cassette capable of expressing a marker (Goldstein and McCusker, 1999, Yeast Chichester Engl. 15, 1541-53; Güldener et al., 2002, Nucleic Acids Res. 30, e23; Güldener et al., 1996, Nucleic Acids Res. 24, 2519-24.; Janke et al., 2004, Yeast 21, 947-62.; Sauer, 1987, Mol. Cell. Biol. 7, 2087-96), at the ends of which the 5' and 3' regions of the target gene are inserted so as to allow the homologous recombination and replace the coding portion of the gene by the expression cassette of the marker.

According to an advantageous embodiment, the fungal microorganism according to the invention is deactivated at the level of the activity involved in the decarboxylation of the hydroxyphenyl pyruvate. In particular, and concerning *S. cerevisiae*, at least 3 genes have been described as being involved in this activity, i.e., ARO10, PDC5 and PDC6 (Hazelwood et al., 2008; Appl. Environ. Microbiol. 74, 2259-66; Kneen et al., 2011, FEBS J. 278, 1842-53; Vuralhan et al., 2005, Appl. Environ. Microbiol. 71, 3276-84.; Vuralhan et al., 2003, Appl. Environ. Microbiol. 69, 4534-41). Advantageously, at least one of the genes encoding phenylpyruvate decarboxylase Aro10, pyruvate decarboxylase PDC5 and pyruvate decarboxylase PDC6 is deactivated. According to a particular embodiment, genes encoding phenylpyruvate decarboxylase Aro10, pyruvate decarboxylase PDC5 and pyruvate decarboxylase PDC6 are deactivated.

Alternatively, the deaminase(s) involved in the first step of the path of breaking down tyrosine are deactivated. In relation to *S. cerevisiae*, this can be deaminase Aro8 and/or deaminase Aro9, or their equivalents in other fungal microorganisms.

Similarly, the alcohol dehydrogenase(s) (denoted ADH) involved in the third step of the path to break tyrosine down into tyrosol can be targeted.

Thus and according to a particular aspect, the present invention seeks a fungal microorganism comprising at least one mutation or deletion in at least one of the genes encoding the following enzymes: deaminase Aro8, deaminase Aro9, decarboxylase Aro10, decarboxylase PDC5, decarboxylase PDC6, alcohol dehydrogenase (ADH). In the scope of the invention, the aforesaid mutations and/or deletion entail a reduction or even the elimination of the capacity of the organism to break tyrosine down into tyrosol, p-hydroxyphenylacetaldehyde and/or p-hydroxyphenylacetate. Advantageously, the aforesaid microorganism also has a capacity to synthesize frambinone from tyrosine, possibly through the introduction of genetic modifications as described above.

According to a particular embodiment, such a microorganism is a strain of *Saccharomyces cerevisiae* which has the capacity to produce frambinone and to inactivate the gene ARO10 encoding a decarboxylase. This microorganism therefore has a path for converting tyrosine into functional frambinone and a limited capacity or no capacity to break tyrosine down into tyrosol, p-hydroxyphenylacetaldehyde and/or p-hydroxyphenylacetate as described above.

For example, this could be the industrial strain RK8, filed with the CNCM on Apr. 26, 2017 under number I-5200. This was obtained from strain RK5, by inserting a cassette allowing inactivation of the ARO10 gene (see examples of implementation below).

According to another aspect, the present invention relates to the use of a fungal microorganism with the capacity to produce the frambinone from tyrosine and a limited capacity or no capacity to break tyrosine down into tyrosol, p-hydroxyphenylacetaldehyde and/or p-hydroxyphenylacetate, advantageously as described above and notably strain I-5200, for the production of frambinone, advantageously by aerobic fermentation.

In other words, the invention also relates to a process for the production of frambinone comprising the culture of a fungal microorganism with the capacity to produce frambinone from tyrosine and a limited capacity or no capacity to break tyrosine down into tyrosol, p-hydroxyphenylacetaldehyde and/or p-hydroxyphenylacetate, advantageously as described above, particularly strain I-5200, in a medium comprising tyrosine. According to a particular embodiment, tyrosine is added into the culture medium at a concentration of between 50 and 450 or 500 mg/L, for example on the order of 300 mg/L. Optionally, the culture medium can also be fortified with coumaric acid and/or phenylalanine.

Alternatively, the microorganism implemented within the invention naturally has a certain capacity to break tyrosine down into tyrosol, p-hydroxyphenylacetaldehyde and/or p-hydroxyphenylacetate, but this path for breaking it down is inhibited by the addition of a repressor to this path, an inhibitor of one of the enzymes involved in this path for instance.

Thus and according to another aspect, the invention relates to a process for the production of frambinone comprising a fungal microorganism culture with the capacity to produce frambinone from tyrosine in a medium consisting of tyrosine and at least one repressor of the path for breaking tyrosine down into tyrosol, p-hydroxyphenylacetaldehyde and/or p-hydroxyphenylacetate. Optionally, it is a microorganism genetically modified to confer or increase the capacity of the organism to produce the frambinone from tyrosine, as described above.

According to a particular embodiment, the microorganism implemented is the industrial strain *Saccharomyces cerevisiae* RK4, registered with the CNCM (National Collection of Microorganism Cultures, Pasteur Institute, 25 rue du Docteur Roux, 75724 Paris Cedex 15) on Jun. 1, 2016 under number I-5101.

Alternatively, the microorganism implemented is the industrial strain *Saccharomyces cerevisae* RK5, registered with the CNCM (National Collection of Microorganism Cultures, Institut Pasteur, 25 rue du Docteur Roux, 75724 Paris Cedex 15) on Apr. 26, 2017 under number I-5199.

According to a particular embodiment, the repressor of the path for breaking tyrosine down into tyrosol, p-hydroxyphenylacetaldehyde and/or p-hydroxyphenylacetate is chosen from among glutamate, glutamine, or one of their derivatives, advantageously glutamate. According to a particular embodiment, said repressor, particularly glutamate, is added into the culture medium at a concentration greater than or equal to 0.5 g/L, even 1, 2 or 3 g/L, on the order of 2 g/L for example.

In the scope of the invention, the fungal microorganism is placed in a culture under conditions favoring the production of frambinone. Conditions particularly suitable for the culture are the following:
  in aerobiosis.
  in a growth medium suitable for fermentation, advantageously an inorganic medium, for example, composed of 1.7 g/L of YNB (Difco™), 5 g/L of ammonium sulfate, 2.7 g/L potassium phosphate and 20 g/L of dextrose;
  from several hours to several days;
  with a pH between 5 and 7, equal to 6 for instance;
  at a temperature between 25° C. and 32° C., equal to 30° C. for instance.

As previously stated and under these conditions, production levels of frambinone were observed that had not previously been achieved, the culture medium showing a concentration of frambinone advantageously greater than 4 mg/L, more advantageously greater than or equal to 5, 6, 7, 8, 9, 10, 11, 12, 13, 14, 15, 16, 17, 18, 19 or even 20, 25 or 30 mg/L.

In a manner known by the person skilled in the art, the frambinone thus produced can be isolated from the culture medium.

The invention will be described in greater detail in the following examples of implementation, supported by the attached figures. These examples of the invention are non-limiting and provided for illustrative purposes only.

Without more precision, it is deemed that the person skilled in the art, using descriptions and examples, will be able to implement and use the microorganisms according to the invention and the methods claimed.

LEGENDS FOR THE FIGURES

FIG. 1: Path for the biosynthesis of frambinone
(1) L-tyrosine (2) p-coumaric acid (3) coumaroyl-CoA (4) p-hydroxybenzalacetone (5) frambinone (6) malonyl-CoA (7) phenylalanine (8) cinnamic acid
TAL: tyrosine ammonia-lyase, 4CL: 4-coumarate-CoA ligase, BAS: benzalacetone synthase, BAR: benzalacetone reductase, PAL: phenylalanine ammonia-lyase, C4H: cinnamate 4 hydroxylase FIG. 2: Path for the biosynthesis of tyrosine This consists of the deamination (Aro8/9) and decarboxylation (Aro10/PDC5/PDC6) steps leading to the formation of p-hydroxyphenylacetaldehyde. The latter may be reduced using an alcohol dehydrogenase (ADH) into tyrosol or oxidized to p-hydroxyphenylacetate. Possible inactivation of the path is indicated by a cross.

Figure 3:
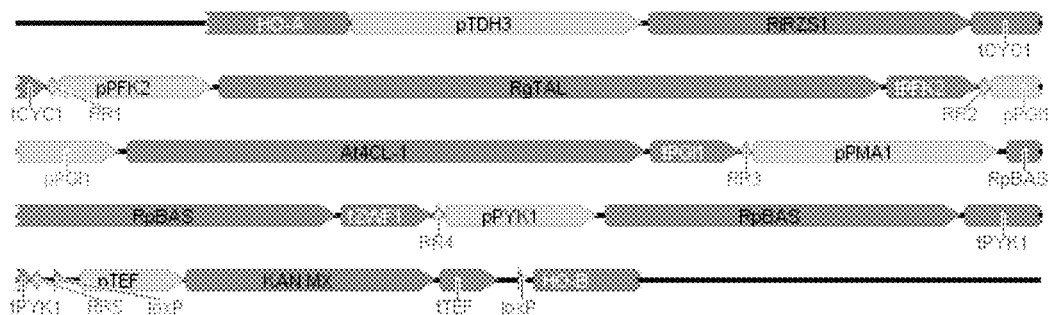
Figure 3:

FIG. 3: Diagram of the HO locus modified in the genome of strains *S. cerevisiae* RK4, RK5 and RK8 and the cassette allowing modification of locus ARO10

A) Diagram of integrated cassettes at HO locus allowing the synthesis of frambinone. Five gene expression cassettes and a marker cassette have been integrated at the level of HO locus by using different regions of overlapping recombination (RR1-5) between the cassettes for the in vivo assembly. In strains RK5 and RK8 the cassette marker (pTEF-KanMX-tTEF) is absent.

B) Diagram of the cassette allowing inactivation of gene ARO10 and conferring resistance to hygromycin.

Figure 4:
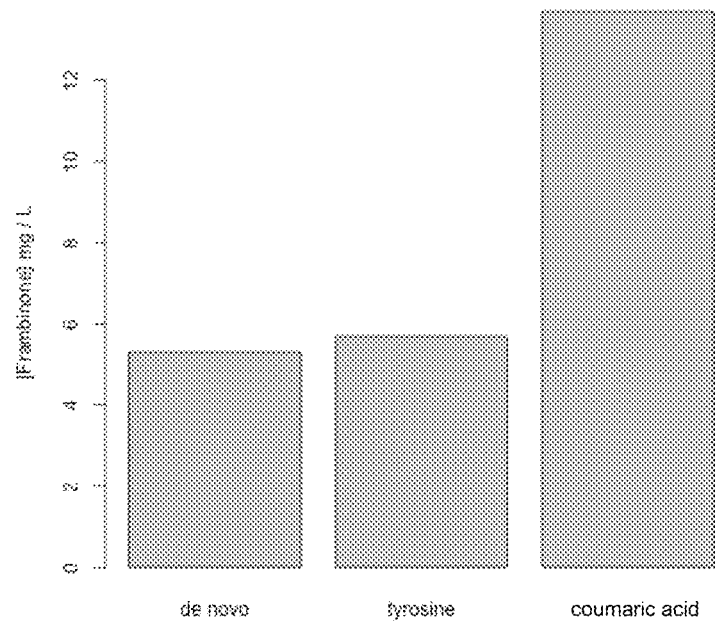

FIG. 4: Production of frambinone by strain *S. cerevisiae* RK4 after 7 days

The concentration of frambinone (mg/L) was determined after 7 days of culture as a function of the substrate (tyrosine synthesized by the cell from glucose and ammonium sulfate (called de novo process), tyrosine or coumaric acid added to the culture medium).

Figure 5:
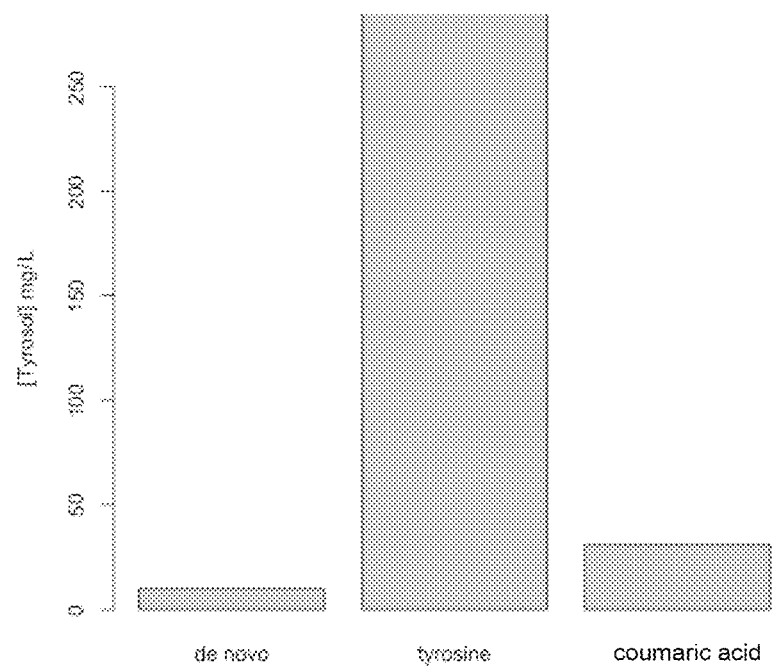

FIG. 5: Production of tyrosol by strain *S. cerevisiae* RK4 after 7 days

The concentration of frambinone (mg/L) was determined after 7 days of culture as a function of the substrate (tyrosine synthesized by the cell from glucose and ammonium sulfate (called de novo process), tyrosine or coumaric acid added to the culture medium).

Figure 6:
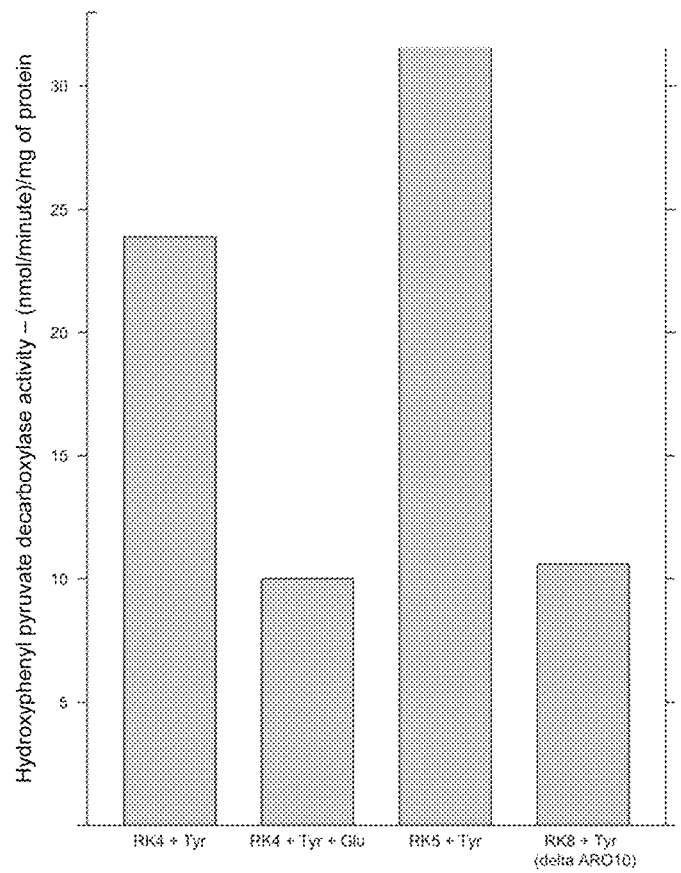

FIG. 6: HDPPC activity in cellular extracts (strain *S. cerevisiae* RK4, RK5 and RK8) after 16 hours of fermentation in the synthetic medium containing tyrosine with or without glutamate The hydroxy-phenylpyruvate (HDPPC) activity (expressed in nmol/min/mg protein) was determined in the cell extract after 16 hours of fermentation in a synthetic medium containing 0.3 g/L of tyrosine and optionally 2 g/L of glutamate.

EXAMPLE EMBODIMENTS

The present invention will be further illustrated with respect to a strain of *Saccharomyces cerevisiae* genetically modified to express 4 heterologous genes encoding enzymes TAL, 4CL, BAS and BAR integrated at its HO locus and effectively producing frambinone from tyrosine in a medium enriched by glutamate, or with a derived strain showing an inactivated ARO10 gene. These examples are in no way limiting.

I) MATERIAL AND METHODS

Generation of Expression Cassettes and Recombinant Strains

To synthesize frambinone from tyrosine, it was chosen to express four heterologous genes in *Saccharomyces cerevisiae* as shown in the Table 4 below:

TABLE 4

Heterologous genes used to establish a path for synthesizing frambinone with *S. cerevisiae*

| Enzyme | Source | Reference | Sequence (codon-optimized for expression with *S. cerevisiae*) |
|---|---|---|---|
| TAL | *Rhodotorula glutinis* | Uniprot P11544 | SEQ ID NO: 5 |
| 4CL | *Arabidopsis thaliana* | Uniprot Q42524 | SEQ ID NO: 8 |
| BAS SA | *Rheum palmatum* | Uniprot Q94FV7 | SEQ ID NO: 11 |
| BAR | *Rubus idaeus* | Uniprot G1FCG0 | SEQ ID NO: 2 |

The encoding sequences were "codon-optimized" with *S. cerevisiae*. The corresponding sequences are shown in Table 4 above.

They were cloned between the proponents and terminators to ensure their expression. Five gene expression cassettes were built (Table 5 below) and, in addition to a cassette marker, were integrated into the genome of industrial strain *S. cerevisiae* filed with the CNCM Sep. 4, 2008 under number I-4071, at the HO locus using the modular cassette integration technique (FIG. 3A). The resulting strain, RK4, was registered with the CNCM (Collection Nationale de Cultures de Microorganismes, Institut Pasteur, 25 rue du Docteur Roux, 75724 Paris Cedex 15) on Jun. 1, 2016, under number I-5101.

TABLE 5

Gene expression cassettes and marker used in strain RK4

| cassette | position of relative integration | Promoter* | SEQ ID NO: | Coding sequence | SEQ ID NO: | Terminator* | SEQ ID NO: |
|---|---|---|---|---|---|---|---|
| BAR | 1 | TDH3 | 1 | RiRZS1 | 2 | CYC1 | 3 |
| TAL | 2 | PFK2 | 4 | RgTAL | 5 | PFK2 | 6 |
| 4CL | 3 | PGI1 | 7 | At4CL-1 | 8 | PGI1 | 9 |
| BAS1 | 4 | PMA1 | 10 | RpBAS | 11 | ZWF1 | 12 |
| BAS2 | 5 | PYK1 | 13 | RpBAS | 11 | PYK1 | 14 |
| marker | 6 | TEF1 | 15 | kanMX | 16 | TEF1 | 17 |

*S. cerevisiae* with the exception of TEF1 (*Ashbya gossypii*)
Ri = *Rubus idaeus*
Rg = *Rhodotorula glutinis*
At = *Arabidopsis thaliana*
Rp = *Rheum palmatum*

From the RK4 strain described above, the RK5 strain was obtained by elimination of the kanMX cassette marker. This was done by expressing the Cre recombinase that leads to excising the kanMX marker which is flanked by loxP sites (Steensma and Linde, 2001, Yeast, 18(5): 469-72). This is the strain registered with the CNCM on Apr. 26, 2017 under number I-5199.

An inactivation cassette of the gene ARO10 was then constructed (FIG. 3B). It is composed of a cassette marker in hygromycin, pTEF1short-HPH-tTEF1 (pTEF1 short: SEQ ID NO: 22; hph: SEQ ID NO: 23; tTEF1: SEQ ID NO: 24), flanked by sequences homologous to the promoter (pARO10: SEQ ID NO: 25) and the terminator (tARO10; SEQ ID NO: 26) of ARO10, both upstream and downstream, respectively. A RNA sequence guide specific to the ARO10 gene has been cloned into a plasmid to express Case9p and said RNA in *S. cerevisiae*. The RK5 strain described above has been co-transformed with this plasmid and the inactivation cassette of gene ARO10. Positive clones (resistant to hygromycin) have been selected and verified for the inactivation of all alleles of ARO10.

The resulting strain RK8 was registered with the CNCM on Apr. 26, 2017 under number I-5200.

HPLC Measurements of the Path's Intermediates and Products

Frambinone, tyrosol and other intermediates of the path were analyzed and quantified by two HPLC methods called "long method" and "ACE_29," respectively. HPLC devices and their parameters are summarized in Table 6 below and allow the separation of the frambinone and tyrosol from other compounds. For quantification, calibration was done with standard solutions between 0.1 and 300 mg/L. The samples of the yeast cultures were centrifuged (>15,000×g, 10 min), and the supernatant filtered through a 0.45 μm filter before injection into the HPLC.

TABLE 6

HPLC devices and parameters

| | Long method | ACE_29 |
|---|---|---|
| HPLC system | Shimadzu LC20AD, PDA detector | |
| Column | Polar Advantage II 3 × 150 mm 3 μm (reverse phase) | C18-PFP [MK] |
| Eluent A | Water + 0.1% formic acid | |
| Eluent B | Methanol | |
| Elution | Isocratic: 82% eluent A and 18% eluent B | Gradient |
| Temperature of the column | 30° C. | |
| Flow Rate | 0.4 mL/min | 0.35 mL/min |
| Injection volume | | 20 μL; |
| Temperature of the automatic sampler | | 10° C. |
| PDA detection | 200-300 nm Quantification at λ 280 nm | 200-400 nm Quantification at λ 280 nm |

Enzymatic Detection of Hydroxyphenyl Pyruvate Decarboxylase (HPPDC) Activity

To quantify the enzymatic activity of the decarboxylation of hydroxyphenyl pyruvate (HPPDC activity), an enzymatic test paired with a crude cell extract has been developed. The cell extract was prepared from an overnight culture (16 h) of the strain of interest in a synthetic medium composed of 1.7 g/L of YNB (Difco™), 5 g/L of ammonium sulfate, 2.7 g/L of potassium phosphate and 20 g/L of dextrose. The environment was also supplemented by 300 mg/L L-tyrosine and optionally different nitrogen sources (for example, L-glutamate). After aerobic growth at 30° C., the cells were harvested by centrifugation (5000×g, 4 min, 4° C.) and washed twice in a wash buffer (10 mM phosphate potassium, 2 mM EDTA, pH 6.8). The packed cell was taken up in an extraction buffer (100 mM potassium phosphate, 2 mM magnesium chloride, 1 mM DTT, 1× cOmplete™ proteinase inhibitors, pH 6.8) and the cells were broken with a "Fast-Prep" disruptor (with 0.45 mm glass beads; four 30 s to 6 m/s cycles, and 1 min on ice). The cell debris was removed by centrifugation and the supernatant used as crude cell extract. The protein concentration was determined using the "Uptima BC Assay Protein Quantification Kit" according to the manufacturer's instructions.

The enzyme assay was carried out as described by Kneen et al. (2011, FEBS J. 278, 1842-53), with minor modifications. The assay couples the HPPDC reaction (decarboxylation of hydroxyphenyl pyruvate (HPP) in hydroxyphenylacetaldehyde) with a second reaction (oxidation of hydroxyphenylacetaldehyde in hydroxyphenyl ethanol/tyrosol) catalyzed by the auxiliary enzyme alcohol dehydrogenase (ADH). The ADH activity leads to reduction of NADH to $NAD^+$ which can be followed thanks to the decrease of absorption at 340 nm in a spectrophotometer. The reaction mixture (1 mL) contained 100 mM potassium phosphate, 1 mM magnesium chloride, 0.5 mM thiamine pyrophosphate, 0.1 mM of NADH, 0.5 U of ADH with horse liver, 4 mM of HPP and the crude cell extract equivalent to approximately 200 μg of total protein. Reactions were measured at 32° C. and pH 6.8. The reaction was initiated by the addition of the substrate HPP.

II/ RESULTS

1/ Production of Frambinone and Other Metabolites from Tyrosine or Coumaric Acid as Substrate by Strain RK4.

Fermentation tests were conducted with strain RK4, cultivated in an inorganic medium composed of 1.7 g/L of YNB (Difco™), 5 g/L of ammonium sulfate, 2.7 g/L of potassium phosphate and 20 g/L of dextrose. Optionally, the medium can contain 300 mg/L of tyrosine or 100 mg/L of coumaric acid. As suggested by Ayuso et al. (2016, Microb. Cell Factories 15. doi:10.1186/s12934-016-0446-2), fermentation tests were conducted under aerobic conditions to optimize the production of frambinone.

As shown in FIG. 4, strain RK4 can synthesize approximately 6 mg/L of frambinone from tyrosine. When coumaric acid is used as substrate, the concentration of frambinone in mediums reaches approximately 14 mg/L. These results are in agreement with those of the prior art and confirm the fact that the production of frambinone from aromatic amino acids is less efficient than from coumaric acid. However, in view of the price of the substrates used for bioconversion, industrial applications are only profitable when tyrosine is used rather than coumaric acid.

A last point of these results concerns the de novo synthesis of frambinone by the constructed strain RK4. Note that the frambinone concentration is approximately the same that observed in the presence of tyrosine. It has been hypothesized that this is probably linked to the regulation of the biosynthesis of tyrosine by extracellular tyrosine, and also to diverting this amino acid by a degradation pathway.

2/ Breaking Tyrosine Down into Tyrosol in Strain RK4

Breaking tyrosine down into tyrosol is a well-known method (FIG. 2) (Hazelwood et al., 2008, Appl. Environ. Microbiol. 74, 2259-66). The first step is transamination of tyrosine resulting in the formation of hydroxyphenyl pyruvate. This compound is then decarboxylated into hydroxyphenylacetaldehyde (EC: 4.1.1.80). Finally, the aldehyde function is reduced to form a hydroxylated molecule called tyrosol (EC: 1.1.1.90).

The production of tyrosol during the fermentation of the strain RK4 was followed. FIG. 5 shows the concentrations of tyrosol in different mediums after 7 days of fermentation. Results confirm that the major part of the tyrosine provided is used for the production of tyrosol.

3/ Inhibition of Hydroxyphenyl Pyruvate Decarboxylase (HPPDC) Activity.

To reduce production of tyrosol in strain RK4, it was decided to inhibit the activity of the enzyme involved in the decarboxylation of hydroxyphenyl pyruvate by adding into the fermentation compounds that reduce HPPDC activity.

Glutamate was selected to be added to the medium to reduce the HPPDC activity. To be certain that adding this supplemental amino acid yields a reduction in enzyme activity, the enzymatic test described above was performed. FIG. 6 shows activity in the cell extraction of RK4 after culture in the fermentation medium containing tyrosine with or without 2 g/L of glutamate. Results confirm reduced HPPDC activity in cells fermenting in the presence of glutamate.

HPPDC activity of strain RK8 was measured at the same time. FIG. 6 states that the deletion of the ARO10 gene encoding for decarboxylase permits the reduction of HPPDC activity in the same proportions as strain RK4 in the presence of glutamate.

FIG. 6 also reveals that, as expected, strains RK4 and RK5 (from which strain RK8 derives) have the same level of HPPDC activity in the presence of tyrosine.

4/ Impact of Inhibition of Breaking Tyrosine Down on the Production of Frambinone and Tyrosol In the first of a series of experiments, the production of tyrosol and frambinone by strain RK4 was followed by HPLC ("Long Method") under both conditions (with or without glutamate). The concentrations of tyrosol observed demonstrate that the reduction of HPPDC activity also reduces the formation of tyrosol: a reduction of 27% in the tyrosol concentration was observed in response to glutamate, in line with the reduction of the HPPDC activity. At the same time, the production of frambinone increased by 40%. This data strongly suggests that the reduction of HPPDC activity reduces the production of tyrosol, thus rendering the tyrosine more available for the frambinone path.

In a second series of experiments, determination of the levels of frambinone (Table 7) and tyrosol (Table 8) produced by the three strains of S. cerevisiae built (RK4, RK5 and RK8) was assessed by HPLC according to the two methods described ("long method" and "ACE_29"). The ACE_29 method uses a new generation column with increased separation and compound resolution abilities, thus reducing the risk of co-elution, notably of frambinone, with other compounds as compared to the "long method".

The results obtained with the "long method" from fermentation in a culture medium containing glutamate show an increase in the frambinone synthesis by the strain RK5 (+58%) compared with fermentation in a culture medium without glutamate, equivalent to strain RK4 under the same conditions. The increases observed equally approach the values of the first series of experiments.

The production of frambinone by strain RK8, cultivated without glutamate, was compared to strain RK5 under the same conditions. A +36% increase in the synthesis of frambinone, around the same observed for strains RK4 and RK5 cultivated with glutamate, was observed.

Determination of the levels of synthesis of frambinone by strains RK4, RK5 and RK8 by using the ACE_29 method similarly shows an increase in the production of frambinone, in proportions, however in higher proportions, that is, +100%, +95% and +129%, respectively.

TABLE 7

Determination by HPLC of the frambinone concentration at the end of fermentation by various strains built into the mediums without glutamate (Glu−) and with glutamate (Glu+).

| Frambinone concentration | Long method | | | | | ACE_29 | | | | |
|---|---|---|---|---|---|---|---|---|---|---|
| (mg/L) | Glu− | MD | Glu+ | MD | Increase | Glu− | MD | Glu+ | MD | Increase |
| RK4 | 4.60 | 0.32 | 7.23 | 0.18 | +57% | 1.09 | 0.17 | 2.17 | 0.02 | +100% |
| RK5 | 4.57 | 0.27 | 7.23 | 0.21 | +58% | 1.14 | 0.02 | 2.21 | 0.03 | +95% |
| RK8 | 6.20 | 0.85 | n.d. | n.d. | +36% | 2.60 | 0.29 | n.d. | n.d. | +129% | n.d.: undetermined
MD: Standard Deviation (SD)

The results obtained using the "long method" from fermentation in a culture medium containing glutamate show an increase in the frambinone synthesis by the strain RK5 (−20%) compared with fermentation in a culture medium without glutamate, equivalent to strain RK4 under the same conditions. The decreases observed equally approach the values of the first series of experiments.

The production of tyrosol by strain RK8, cultivated without glutamate, was compared to strain RK5 under the same conditions. A −49% decrease in the synthesis of tyrosol, around the same observed for strains RK4 and RK5 cultivated with glutamate, was observed.

Determination of the levels of synthesis of frambinone by strains RK4, RK5 and RK8 using the ACE_29 method similarly shows a decrease in the production of tyrosol in similar proportions, that is, −19%, −19% and −52%, respectively.

TABLE 8

HPLC determination of the tyrosol concentration at the end of fermentation by various strains built into the mediums without (Glu−) and with (Glu+) glutamate.

| Concentration In tyrosol | Long method | | | | | ACE_29 | | | | |
|---|---|---|---|---|---|---|---|---|---|---|
| (mg/L) | Glu− | MD | Glu+ | MD | Decrease | Glu− | MD | Glu+ | MD | Decrease |
| RK4 | 158.8 | 0.3 | 128.7 | 2.2 | −19% | 184.2 | 4.4 | 149.2 | 2.5 | −19% |
| RK5 | 158.8 | 0.6 | 127.4 | 0.5 | −20% | 183.9 | 1.0 | 149.4 | 1.9 | −19% |
| RK8 | 80.3 | 4.3 | n.d. | n.d. | −49% | 88.3 | 5.9 | n.d. | n.d. | −52% | n.d.: undetermined
MD: standard deviation (SD)

III/ CONCLUSIONS

In conclusion, introduction of the frambinone path as shown in FIG. 1 is sufficient to produce frambinone from tyrosine by means of S. cerevisiae. However, when tyrosine is added to the fermentation medium, the bioconversion is not very effective and leads to the production of a large quantity of by-products, essentially tyrosol as reported above. To reduce "hijacking" the substrate, the HPPDC activity involved in breaking tyrosine down into tyrosol was successfully reduced by adding an inhibitor of said enzyme activity or the inactivation of gene ARO10. As reported, this allowed the production of frambinone to be increased. Alternatively, other strategies can be used, such as the selection of a microbial strain with very low HPPDC activity, based on a natural genetic background or via the introduction of other genetic modifications such as the deletion of the genes encoding the HPPDC enzymes.

The invention claimed is:

1. A process for the production of frambinone comprising culturing a genetically modified fungal microorganism with a capacity to produce frambinone from tyrosine in a medium comprising tyrosine and a repressor of the path for breaking tyrosine down into tyrosol, p-hydroxyphenylacetaldehyde and/or p-hydroxyphenylacetate, and wherein the repressor is glutamate.

2. The process for the production of frambinone according to claim 1 characterized in that the microorganism
   (a) belongs to the phyla chosen from among the ascomycetes or basidiomycetes,
   (b) includes at least one heterologous sequence encoding the enzyme 4-coumarate: CoA ligase (4CL) or benzalacetone synthase (BAS),
   (c) comprises at least one heterologous or supernumerary sequence encoding the enzyme tyrosine ammonia lyase (TAL) or benzalacetone reductase (BAR),
   (d) comprises at least one heterologous or supernumerary sequence encoding the enzyme phenylalanine ammonia lyase (PAL) or cinnamate 4 hydroxylase (C4H), or
   (e) comprises any combination of characteristics (a)-(d).

3. The process for the production of frambinone according to claim 1 characterized in that the microorganism is the industrial strain *Saccharomyces cerevisiae* RK4 registered with the CNCM on Jun. 1, 2016 under number I-5101.

4. The process for the production of frambinone according to claim 1 characterized in that the microorganism is the industrial strain *Saccharomyces cerevisiae* RK5 registered with the CNCM on Apr. 26, 2017 under number I-5199.

5. The process for the production of frambinone according to claim 1 characterized in that the microorganism belongs to the genus *Yarrowia, Debaryomyces, Arxula, Scheffersomyces, Geotrichum, Pichia,* or *Saccharomyces.*

6. The process for the production of frambinone of claim 2 characterized in that the microorganism includes at least one heterologous sequence encoding 4CL and BAS, at least one heterologous or supernumerary sequence encoding TAL and BAR, and/or at least one heterologous or supernumerary sequence encoding PAL or C4H.

* * * * *

SEQUENCE LISTING

```
<160> NUMBER OF SEQ ID NOS: 26

<210> SEQ ID NO 1
<211> LENGTH: 962
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "TDH3 promoter (S. cerevisiae)"

<400> SEQUENCE: 1
tcctatgact tgatgcaaat tcccaaagct aataacatgc aagacacgta cggtcaagaa      60
gacatatttg acctcttaac aggttcagac gcgactgcct catcagtaag acccgttgaa     120
aagaacttac ctgaaaaaaa cgaatatata ctagcgttga atgttagcgt caacaacaag     180
aagtttaatg acgcggaggc caaggcaaaa agattccttg attacgtaag ggagttagaa     240
tcattttgaa taaaaaacac gcttttttcag ttcgagttta tcattatcaa tactgccatt     300
tcaaagaata cgtaaataat taatagtagt gattttccta actttattta gtcaaaaaat     360
tagcctttta attctgctgt aacccgtaca tgcccaaaat aggggggcggg ttacacagaa     420 tatataacat cgtaggtgtc tgggtgaaca gtttattcct ggcatccact aaatataatg     480
gagcccgctt tttaagctgg catccagaaa aaaaaagaat cccagcacca aaatattgtt     540
ttcttcacca accatcagtt cataggtcca ttctcttagc gcaactacag agaacagggg     600
cacaaacagg caaaaaacgg gcacaacctc aatggagtga tgcaacctgc ctggagtaaa     660
tgatgacaca aggcaattga cccacgcatg tatctatctc attttcttac accttctatt     720
accttctgct ctctctgatt tggaaaaagc tgaaaaaaaa ggttgaaacc agttccctga     780
aattattccc ctacttgact aataagtata taagacggt aggtattgat tgtaattctg     840
taaatctatt tcttaaactt cttaaattct acttttatag ttagtctttt ttttagtttt     900
aaaacaccaa gaacttagtt tcgaataaac acacataaac aaacaaacct gcaggttata     960
aa                                                                     962
```

<210> SEQ ID NO 2
<211> LENGTH: 1047
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "codon-optimized coding sequence of RZS1 from R. idaeus"

<400> SEQUENCE: 2

```
atggcttctg gtggtgaaat gcaagtctct aacaagcaag ttatcttcag agattacgtt      60
accggtttcc caaaagaatc cgatatggaa ttgaccacca gatccattac tttgaaattg     120
ccacaaggtt ctaccggttt gttgttgaaa aacttgtact tgtcttgcga cccttacatg     180
agagctagaa tgactaatca tcacagattg tcctacgtcg attcttttaa accaggttcc     240
ccaattattg ttacggtgt tgctagagtt ttggaatctg gtaatccaaa gtttaaccca     300
ggtgatttgg tttggggttt tactggttgg gaagaatact ctgttattac cgctactgaa     360
tccttgttca agatccataa taccgatgtc ccattgtctt actacactgg tttgttgggt     420
atgccaggta tgactgctta tgctggtttt tacgaaattt gctctccaaa aaagggtgaa     480
accgtttatg tttctgctgc ttcaggtgct gttggtcaat tggtcggtca atttgctaag     540
ttgactggtt gttatgttgt tggttctgcc ggttctaaag aaaaggttga tttgttgaag     600
aacaagttcg gtttcgatga agccttcaac tacaagaag aagctgattt ggacgctgct     660
ttgagaagat attttccaga tggtatcgac atctacttcg aaaatgttgg tggtaagatg     720
ttggatgctg ttttgccaaa tatgagacca aagggtagaa ttgctgtttg cggtatgatt     780
tcccaataca acttggaaca accagaaggt gttagaaact tgatggcttt gatcgttaag     840
caagtcagaa tggaaggttt catggttttc tcttactacc acttgtacgg taaattcttg     900
gaaactgtct tgccttacat caagcaaggt aagattacct acgttgaaga tgttgttgat     960
ggtttggata tgctccagc tgctttaatt ggtttgtact ctggtagaaa cgtcggtaag    1020
caagttgttg ttgtttccag agaataa                                         1047
```

<210> SEQ ID NO 3
<211> LENGTH: 327
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "CYC1 terminator (S. cerevisiae)"

<400> SEQUENCE: 3

```
ggcgcgccac gtccgacggc ggcccgacgg gtccgaggcc tcggagatcc gtccccttt      60
tcctttgtcg atatcatgta attagttatg tcacgcttac attcacgccc tccccccaca    120
tccgctctaa ccgaaaagga aggagttaga caacctgaag tctaggtccc tatttatttt    180
tttatagtta tgttagtatt aagaacgtta tttatatttc aaatttttct ttttttttctg    240
tacagacgcg tgtacgcatg taacattata ctgaaaacct tgcttgagaa ggttttggga    300
cgctcgaagg ctttaatttg caagctg                                          327
```

<210> SEQ ID NO 4
<211> LENGTH: 521
<212> TYPE: DNA

<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "PFK2 promoter (S. cerevisiae)"

<400> SEQUENCE: 4

```
agagccgatt agtggaagcc acggttacgt gattgcggtt ttttttttcct acgtataacg      60
ctatgacggt agttgaatgt taaaaacgaa aacagagata ttgaattgat caatttgatc     120
agtacgtatg taatcttttg tttgccatgt taaatcggcc tttttttcca tccggtcttt     180
atcgaccatt catttattac atcgcaatga agtctctcgc ttcatgttgt tgttttttt      240
cctgcctttt ttttatccgc tctcattctt attttttccta cttgcatttt ataaaacaat     300
aatatttttt tcttcttttt gtcctttatt tattacttcc ttgattaaaa gcttcttatc     360
ttcggtttca taaagaagaa aattcctttt tttttttttt tttccttctt cttgcttaaa     420
agcctttctt atatctcatt tgaacaatag aactagattt agagactagt ttagcattgg     480
ccaagaacta accatacgca aaacaacctg caggttataa a                         521
```

<210> SEQ ID NO 5
<211> LENGTH: 2151
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "codon-optimized coding sequence of TAL1 from R. glutinis"

<400> SEQUENCE: 5

```
atggctccat ccttggattc catctctcat tcttttgcta atggtgttgc ttctgctaag      60
caagctgtta atggtgcttc tactaatttg gctgttgctg ttctcatttt gccaactact    120
caagttacac aagttgacat cgtcgaaaaa atgttggctg ctccaactga ttctaccttg    180
gaattggatg ttactctttt gaacttgggt gatgttgttt ctgctgctag aaaaggtaga    240
ccagttagag ttaaggattc cgacgaaatc agatccaaga tcgataagtc tgtcgaattc    300
ttgagatccc aattgtccat gtctgtttac ggtgttacta ctggttttgg tggttctgct    360
gatacaagaa ctgaagatgc tatctccttg caaaaggctt gttggaaca tcaattgtgt    420
ggtgttttgc catcctcatt cgattctttt agattgggta gaggtttgga aaactccttg    480
ccattggaag ttgttagagg tgctatgact attagagtca actctttgac tagaggtcat    540
tccgctgtta gattggttgt tttggaagct tgaccaact tcttgaacca tggtattact    600
ccaatcgttc cattgagagg tactatttct gcttctggtg atttgtctcc attgtcttat    660
attgctgctg ccatttctgg tcatccagat tctaaagttc atgttgtcca cgaaggtaaa    720
gaaaagatct tgtatgctag aaagctatg gccttgttta acttggaacc agttgtttta    780
ggtccaaaag aaggtttggg tttggttaat ggtactgctg tttcagcttc tatggctact    840
ttggctttac atgatgctca catgttgtct tgttgtcccc aatctttgac tgctatgaca    900
gttgaagcaa tggttggtca tgctggttca tttcatccat tcttgcatga tgttactaga    960
ccacatccaa cccaaattga agttgctggt aacatcagaa agttgttgga aggttctaga   1020
ttcgccgttc atcatgaaga agaagttaag gttaaggacg acgaaggtat cttgagacaa   1080
gatagatacc cattgagaac ttctccacaa tggttaggtc cattggtttc cgatttgatt   1140
```

```
catgctcatg ctgttttgac tattgaagct ggtcaatcta ctaccgataa cccattgatt    1200
gatgtcgaaa acaagacctc tcatcatggt ggtaattttc aagctgctgc tgttgctaac    1260
actatggaaa aaactagatt aggtttggcc caaatcggta agttgaactt cactcaattg    1320
accgaaatgt tgaacgctgg tatgaataga ggtttaccat cttgtttggc tgctgaagat    1380
ccatctttat cttaccattg caagggtttg atattgccg ctgctgctta tacttctgaa    1440
ttgggtcatt tggctaaccc agttactact catgttcaac cagctgaaat ggctaatcaa    1500
gcagttaact cattggcttt gatttccgct agaagaacta ccgaatctaa cgatgttttg    1560
tccttgttgt tggctactca cttgtattgc gttttacaag ccattgattt gagagccatc    1620
gaatttgaat tcaagaagca atttggtcca gccatcgttt ccttgattga tcaacatttt    1680
ggttccgcta tgaccggttc taatttgaga gatgaattgg tcgaaaaggt caacaagact    1740
ttggctaaga gattggaaca aactaactcc tacgatttgg ttcctagatg gcatgatgct    1800
ttttcatttg ctgctggtac tgttgttgaa gtcttgtcat ctacatcttt gtctttggct    1860
gcagttaacg cttggaaagt tgctgcagct gaatctgcta tttctttgac aagacaagtc    1920
agagaaactt tctggtctgc tgcttctaca tcatctccag ctttgtcata cttgtctcca    1980
agaactcaaa tcttgtacgc cttcgttaga aagaattgg gtgttaaggc tagaagaggt    2040 gatgttttt tgggtaagca agaagttacc atcggttcca atgtttccaa aatctacgaa    2100
gccattaagt ccggtagaat caacaacgtt tgttgaaga tgttggctta a            2151

<210> SEQ ID NO 6
<211> LENGTH: 309
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "PFK2 terminator (S. cerevisiae)"

<400> SEQUENCE: 6
ggcgcgccta gcaaaatgac cttttattac actttctatt attaatgtca attaatgtta     60
acccatgttt ttcttttgtg tctataattc ttttttttta tctctaagct tttgaacaat    120
gaattttttg ttcctttctt ttaataatac aagtactacc ccatgaaacc aatattatca    180 tgcatttta tgaatgtcaa gaataaagat actgttattt tttgtgtctt atttttttc    240 tctttgttta tttaaacgtt ttctaaaatt aaaacttatg tatactggaa tatgtgatat    300
agacgattt                                                             309

<210> SEQ ID NO 7
<211> LENGTH: 521
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "PGI1 promoter (S. cerevisiae)"

<400> SEQUENCE: 7
gttgaactat gttgtgccag cgtaacatta aaaagagtg tacaaggcca cgttctgtca      60
ccgtcagaaa aatatgtcaa tgaggcaaga accgggatgg taacaaaaat cacgatctgg    120
gtgggtgtgg gtgtattgga ttataggaag ccacgcgctc aacctggaat tacaggaagc    180
tggtaatttt ttgggtttgc aatcatcacc atctgcacgt tgttataatg tcccgtgtct    240
```

| | |
|---|---|
| atatatatcc attgacggta ttctattttt ttgctattga aatgagcgtt ttttgttact | 300 |
| acaattggtt ttacagacgg aatttttccct atttgtttcg tcccattttt ccttttctca | 360 |
| ttgttctcat atcttaaaaa ggtcctttct tcataatcaa tgctttcttt tacttaatat | 420 |
| tttacttgca ttcagtgaat tttaatacat attcctctag tcttgcaaaa tcgatttaga | 480 |
| atcaagatac cagcctaaaa aaacaacctg caggttataa a | 521 |

<210> SEQ ID NO 8
<211> LENGTH: 1686
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "codon-optimized coding sequence of 4CL-1 from
    A. thaliana"

<400> SEQUENCE: 8

| | |
|---|---|
| atggctccac aagaacaagc tgtttctcaa gttatggaaa agcaatccaa caacaacaac | 60 |
| tccgatgtca tcttcagatc taagttgcca gatatctaca tcccaaaacca tttgtccttg | 120 |
| cacgattaca tcttccaaaa catttctgaa ttcgctacca agccatgctt gattaacggt | 180 |
| ccaactggtc atgtttacac ctactctgat gttcacgtta tctccagaca aattgctgct | 240 |
| aactttcaca gttgggtgt caatcaaaac gatgtcgtta tgttgttgtt gccaaactgt | 300 |
| ccagaattcg tcttgtcttt tttggctgct tcttttagag gtgctactgc tactgctgct | 360 |
| aatccatttt ttactccagc tgaaattgct aagcaagcta aggcttctaa caccaagttg | 420 |
| attattaccg aagctagata cgtcgacaag atcaagccat gcaaaatga tgatggtgtt | 480 |
| gttatcgtct gcatcgatga taatgaatcc gttccaattc agaaggttg tttgagattc | 540 |
| actgaattga ctcaatctac taccgaagcc tccgaagtta ttgattccgt tgaaatttct | 600 |
| ccagatgatg ttgttgctttt gccatactct tcaggtacta ctggtttgcc aaaaggtgtt | 660 |
| atgttgactc ataagggttt ggttacatcc gttgctcaac aagttgatgg tgaaaatcca | 720 |
| aacttgtact ccactccga tgatgttatt ttgtgcgttt tgccaatgtt ccatatctac | 780 |
| gccttgaact ctattatgtt gtgcggtttg agagttggtg ctgccatttt gattatgcca | 840 |
| aagttcgaaa tcaatttgtt gttggaattg atccaaagat gcaaggttac tgttgctcca | 900 |
| atggttccac aatagttttt ggctattgcc aaatcttctg aaaccgaaaa gtacgacttg | 960 |
| tcctctatca gagttgttaa gtctggtgct gctccattgg gtaaagaatt ggaagatgct | 1020 |
| gttaatgcca gttcccaaa tgctaaattg ggtcaaggtt acggtatgac tgaagctggt | 1080 |
| ccagttttag ctatgtcttt gggttttgct aaagaaccat tcccagttaa gtcaggtgct | 1140 |
| tgtggtactg ttgttagaaa tgctgaaatg aagatcgttg atccagatac cggtgattcc | 1200 |
| ttgtctagaa atcaaccagg tgaaatctgc atcagaggtc atcaaattat gaagggttac | 1260 |
| ttgaacaatc cagctgctac agctgaaacc attgataagg atggttggtt gcatactggt | 1320 |
| gatattggtt tgatcgatga tgacgacgaa ttattcatcg tcgatagatt gaaagaattg | 1380 |
| atcaagtaca agggtttcca agttgctcca gctgaattgg aagctttgtt gattggtcat | 1440 |
| ccagatatta ccgatgttgc tgttgttgct atgaaggaag aagctgctgg tgaagttcca | 1500 |
| gttgcttttg ttgttaagtc caaggactct gaattgtccg aagatgatgt taagcaattc | 1560 |
| gtcagtaagc aagtcgtttt ctacaagaga atcaacaagg ttttcttcac cgaatccatt | 1620 |

```
ccaaaagctc catctggtaa gatcttgaga aaagatttga gagctaagtt ggccaacggt    1680
ttgtga                                                               1686

<210> SEQ ID NO 9
<211> LENGTH: 304
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "PGI1 terminator (S. cerevisiae)"

<400> SEQUENCE: 9
ggcgcgccta gcacaaatcg ctcttaaata tatacctaaa gaacattaaa gctatattat      60
aagcaaagat acgtaaattt tgcttatatt attatacaca tatcatattt ctatattttt     120
aagatttggt tatataatgt acgtaatgca aaggaaataa attttataca ttattgaaca     180
gcgtccaagt aactacatta tgtgcactaa tagtttagcg tcgtgaagac tttattgtgt     240
cgcgaaaagt aaaaatttta aaaattagag caccttgaac ttgcgaaaaa ggttctcatc     300
aact                                                                  304

<210> SEQ ID NO 10
<211> LENGTH: 821
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "PMA1 promoter (S. cerevisiae)"

<400> SEQUENCE: 10
aacggagaaa cataaacagg cattgctggg atcacccata catcactctg ttttgcctga      60
ccttttccgg taatttgaaa acaaacccgg tctcgaagcg gagatccggc gataattacc     120
gcagaaataa acccatacac gagacgtaga accagccgca catggccgga gaaactcctg     180
cgagaatttc gtaaactcgc gcgcattgca tctgtatttc ctaatgttta tccattgctt     240
ttttgttgtc ttttttccctc gttcacagaa agtctgaaga agctatagta gaactatgag     300
ctttttttgt ttctgttttc cttttttttt ttttacctc tgtggaaatt gttactctca     360
cactctttag ttcgtttgtt tgttttgttt attccaatta tgaccggtga cgaaacgtgg     420
tcgatggtgg gtaccgctta tgctcccctc cattagtttc gattatataa aaaggccaaa     480
tattgtatta ttttcaaatg tcctatcatt atcgtctaac atctaatttc tcttaaattt     540
tttctctttc tttcctataa caccaatagt gaaaatcttt ttttcttcta tatctacaaa     600 aactttttt ttctatcaac ctcgttgata aattttttct ttaacaatcg ttaataatta     660
attaattgga aaataaccat ttttttctctc ttttatacac acattcaaaa gaaagaaaaa     720
aaatataccc cagctagtta aagaaaatca ttgaaaagaa taagaagata agaaagattt     780
aattatcaaa caatatcaat aaacaacctg caggttataa a                          821

<210> SEQ ID NO 11
<211> LENGTH: 1155
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
```

<223> OTHER INFORMATION: "codon-optimized coding sequence of BAS from R.
palmatum"

<400> SEQUENCE: 11

```
atggctaccg aagaaatgaa gaaattggct accgttatgg ctattggtac tgctaatcca      60
ccaaactgtt attaccaagc tgatttccca gacttctact tcagagttac caactctgat     120
cacttgatca acttgaagca aaagttcaag agattgtgcg aaaactccag aatcgaaaag     180
agatacttgc acgtcactga gaaaatcttg aagaaaacc caaacattgc tgcttacgaa      240
gctacttctt tgaacgttag acataagatg caagttaagg gtgttgccga attgggtaaa     300
gaagctgctt gaaaagcaat caagaatgg ggtcaaccta gtccaagat acccatttg        360
atcgtttgtt gtttggccgg tgttgatatg ccaggtgctg attatcaatt gaccaagttg     420
ttggatttgg acccatctgt taagagattc atgttctacc atttggttg ttatgctggt      480
ggtactgttt tgagattggc taaggatatt gccgaaaaca caagggtgc tagagttttg      540
attgtctgtt ctgaaatgac taccacctgt tttagaggtc catctgaaac tcatttggac    600
tccatgattg gtcaagctat tttgggtgat ggtgctgctg ctgttatagt tggtgctgat   660
ccagatttga ctgttgaaag accaatcttc gaattggttt ctactgctca aactatcgtt    720
ccagaatctc atggtgctat tgaaggtcat tgttggaat ctggtttgtc cttccacttg     780
tacaaaactg ttccaacctt gatctccaac aacattaaga cctgtttgtc tgatgctttc    840
accccattga atatctctga ttggaattcc ttgttctgga ttgctcatcc aggtggtcca   900
gcaattttgg atcaagttac tgctaaagtt ggtttggaaa agaaaagtt gaaggttacc   960
agacaagtct tgaaggatta cggtaatatg tcctctgcta ccgttttttt catcatggac  1020
gaaatgagaa aaagtccctt ggaaaatggt caagccacta ctggtgaagg tttggaatgg 1080
ggtgttttgt ttggttttgg tccaggtatt accgttgaaa ctgttgtctt gagatccgtt 1140
ccagttatct cttaa                                                  1155
```

<210> SEQ ID NO 12
<211> LENGTH: 311
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "ZWF1 terminator (S. cerevisiae)"

<400> SEQUENCE: 12

```
ggcgcgccta gcaaaaatgc aagcacattc atttatcggc taagtcactg aaatttttt      60
ttttcgagtg attttatctt gcaagctcac tctccttgtt cttttctcct ctataatggc     120
atcttccccc gcccaccaac tcctctctac ttgcgtgtgt atttgtttgt atacatgtgt     180
aaatatatat acataaaaga atgtcgtctc atgtattttt taactttag ccgcggtcag    240
tgacattttg gctttcccac cattccacgt ctgaaaaaaa aaaaagaga taaaatatga    300
attgaatata t                                                        311
```

<210> SEQ ID NO 13
<211> LENGTH: 517
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "PYK1 promoter (S. cerevisiae)"

<400> SEQUENCE: 13

```
acagattggg agattttcat agtagagttc agcatgatag ctacgtaaat gtgttccgca    60
ccgtcacaaa gtgttttcta ctgttctttc ttctttcgtt cattcagttg agttgagtga   120
gtgctttgtt caatggatct tagctaaaat gcatattttt tctcttggta aatgaatgct   180
tgtgatgtct tccaagtgat ttcctttcct tcccatatga tgctaggtac ctttagtgtc   240
ttcctgaaaa aaaaggctcg ccatcaaaac gatattcgtt ggcttttttt tctgaattat   300
aaatactctt tagtaacttt ccatttctaa gaacctcttt tttccagtta tatcatggtc   360
cccttttcaaa gttattctct actctttttc atattcattc ttttttcatcc tttggtttt   420
tattcttaac ttgtttatta ttctctcttg tttctattta caagacacca atcaaaacaa   480
ataaaacatc atcacaaaac aacctgcagg ttataaa                            517
```

<210> SEQ ID NO 14
<211> LENGTH: 312
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "PYK1 terminator (S. cerevisiae)"

<400> SEQUENCE: 14

```
ggcgcgccta gcaaaaagaa tcatgattga atgaagatat tatttttttg aattatattt    60
tttaattttt atataaagac atggttttc ttttcaactc aaataaagat ttataagtta   120
cttaaataac atacattta taaggtattc tataaaaga gtattatgtt attgttaacc    180
ttttttgtctc caattgtcgt cataacgatg aggtgttgca ttttttggaaa cgagattgac   240
atagagtcaa aatttgctaa atttgatccc tcccatcgca agataatctt ccctcaaggt   300
tatcatgatt at                                                        312
```

<210> SEQ ID NO 15
<211> LENGTH: 344
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "TEF1 promoter (A. gossypii)"

<400> SEQUENCE: 15

```
gacatggagg cccagaatac cctccttgac agtcttgacg tgcgcagctc agggggcatga    60
tgtgactgtc gcccgtacat ttagcccata catccccatg tataatcatt tgcatccata   120
cattttgatg gccgcacggc gcgaagcaaa aattacggct cctcgctgca gacctgcgag   180
cagggaaacg ctcccctcac agacgcgttg aattgtcccc acgccgcgcc cctgtagaga   240
aatataaaag gttaggattt gccactgagg ttcttctttc atatacttcc ttttaaaatc   300
ttgctaggat acagttctca catcacatcc gaacataaac aacc                    344
```

<210> SEQ ID NO 16
<211> LENGTH: 810
<212> TYPE: DNA
<213> ORGANISM: Artificial Sequence
<220> FEATURE:
<223> OTHER INFORMATION: Synthetic Polynucleotide

```
<220> FEATURE:
<221> NAME/KEY: misc_feature
<223> OTHER INFORMATION: "coding sequence of a kanamycin resistance gene
      kanR (from E. coli transposon Tn903)"

<400> SEQUENCE: 16
atgggtaagg aaaagactca cgtttcgagg ccgcgattaa attccaacat ggatgctgat    60
ttatatgggt ataaatgggc tcgcgataat gtcgggcaat caggtgcgac aatctatcga   120
ttgtatggga agcccgatgc gccagagttg tttctgaaac atggcaaagg tagcgttgcc   180
aatgatgtta cagatgagat ggtcagacta aactggctga cggaatttat gcctcttccg   240
accatcaagc attttatccg tactcctgat gatgcatggt tactcaccac tgcgatcccc   300
ggcaaaacag cattccaggt attagaagaa tatcctgatt caggtgaaaa tattgttgat   360
gcgctggcag tgttcctgcg ccggttgcat tcgattcctg tttgtaattg tccttttaac   420
agcgatcgcg tatttcgtct cgctcaggcg caatcacgaa tgaataacgg tttggttgat   480
gcgagtgatt ttgatgacga gcgtaatggc tggcctgttg aacaagtctg gaaagaaatg   540
cataagcttt tgccattctc accggattca gtcgtcactc atggtgattt ctcacttgat   600
aaccttattt ttgacgaggg gaaattaata ggttgtattg atgttggacg agtcggaatc   660
gcagaccgat accaggatct tgccatccta tggaactgcc tcggtgagtt ttctccttca   720
ttacagaaac ggctttttca aaaatatggt attgataatc ctgatatgaa taaattgcag   780
tttcatttga tgctcgatga gttttttctaa                                   810

<210> SEQ ID NO 17
<211> LENGTH: 203
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "TEF1 terminator (A. gossypii)"

<400> SEQUENCE: 17
tcagtactga caataaaaag attcttgttt tcaagaactt gtcatttgta tagttttttt    60
atattgtagt tgttctattt taatcaaatg ttagcgtgat ttatattttt tttcgcctcg   120
acatcatctg cccagatgcg aagttaagtg cgcagaaagt aatatcatgc gtcaatcgta   180
tgtgaatgct ggtcgctata ctg                                          203

<210> SEQ ID NO 18
<211> LENGTH: 713
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<223> OTHER INFORMATION: "R. glutinis TAL1 (P11544)"

<400> SEQUENCE: 18
```

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly

```
            50                  55                  60
Tyr Ser Leu Asn Leu Gly Asp Val Val Ser Ala Ala Arg Lys Gly Arg
 65                  70                  75                  80

Pro Val Arg Val Lys Asp Ser Asp Glu Ile Arg Ser Lys Ile Asp Lys
                 85                  90                  95

Ser Val Glu Phe Leu Arg Ser Gln Leu Ser Met Ser Val Tyr Gly Val
                100                 105                 110

Thr Thr Gly Phe Gly Gly Ser Ala Asp Thr Arg Thr Glu Asp Ala Ile
                115                 120                 125

Ser Leu Gln Lys Ala Leu Leu Glu His Gln Leu Cys Gly Val Leu Pro
130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
                180                 185                 190

Asn Phe Leu Asn His Gly Ile Thr Pro Ile Val Pro Leu Arg Gly Thr
                195                 200                 205

Ile Ser Ala Ser Gly Asp Leu Ser Pro Leu Ser Tyr Ile Ala Ala Ala
210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
                260                 265                 270

Ala Val Ser Ala Ser Met Ala Thr Leu Ala Leu His Asp Ala His Met
                275                 280                 285

Leu Ser Leu Leu Ser Gln Ser Leu Thr Ala Met Thr Val Glu Ala Met
290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Val Lys Val Lys
                340                 345                 350

Asp Asp Glu Gly Ile Leu Arg Gln Asp Arg Tyr Pro Leu Arg Thr Ser
                355                 360                 365

Pro Gln Trp Leu Gly Pro Leu Val Ser Asp Leu Ile His Ala His Ala
                370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
                420                 425                 430

Gly Lys Leu Asn Phe Thr Gln Leu Thr Glu Met Leu Asn Ala Gly Met
                435                 440                 445

Asn Arg Gly Leu Pro Ser Cys Leu Ala Ala Glu Asp Pro Ser Leu Ser
                450                 455                 460

Tyr His Cys Lys Gly Leu Asp Ile Ala Ala Ala Ala Tyr Thr Ser Glu
465                 470                 475                 480
```

```
Leu Gly His Leu Ala Asn Pro Val Thr Thr His Val Gln Pro Ala Glu
            485                 490                 495

Met Ala Asn Gln Ala Val Asn Ser Leu Ala Leu Ile Ser Ala Arg Arg
        500                 505                 510

Thr Thr Glu Ser Asn Asp Val Leu Ser Leu Leu Leu Ala Thr His Leu
        515                 520                 525

Tyr Cys Val Leu Gln Ala Ile Asp Leu Arg Ala Ile Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys
705                 710

<210> SEQ ID NO 19
<211> LENGTH: 561
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<223> OTHER INFORMATION: "A. thaliana 4CL1 (Q42524 ou AAA82888.1)"

<400> SEQUENCE: 19

Met Ala Pro Gln Glu Gln Ala Val Ser Gln Val Met Glu Lys Gln Ser
1               5                   10                  15

Asn Asn Asn Asn Ser Asp Val Ile Phe Arg Ser Lys Leu Pro Asp Ile
            20                  25                  30

Tyr Ile Pro Asn His Leu Ser Leu His Asp Tyr Ile Phe Gln Asn Ile
        35                  40                  45

Ser Glu Phe Ala Thr Lys Pro Cys Leu Ile Asn Gly Pro Thr Gly His
    50                  55                  60

Val Tyr Thr Tyr Ser Asp Val His Val Ile Ser Arg Gln Ile Ala Ala
65                  70                  75                  80

Asn Phe His Lys Leu Gly Val Asn Gln Asn Asp Val Val Met Leu Leu
                85                  90                  95

Leu Pro Asn Cys Pro Glu Phe Val Leu Ser Phe Leu Ala Ala Ser Phe
            100                 105                 110
```

```
Arg Gly Ala Thr Ala Thr Ala Ala Asn Pro Phe Phe Thr Pro Ala Glu
        115                 120                 125

Ile Ala Lys Gln Ala Lys Ala Ser Asn Thr Lys Leu Ile Ile Thr Glu
130                 135                 140

Ala Arg Tyr Val Asp Lys Ile Lys Pro Leu Gln Asn Asp Asp Gly Val
145                 150                 155                 160

Val Ile Val Cys Ile Asp Asp Asn Glu Ser Val Pro Ile Pro Glu Gly
                165                 170                 175

Cys Leu Arg Phe Thr Glu Leu Thr Gln Ser Thr Thr Glu Ala Ser Glu
            180                 185                 190

Val Ile Asp Ser Val Glu Ile Ser Pro Asp Val Val Ala Leu Pro
        195                 200                 205

Tyr Ser Ser Gly Thr Thr Gly Leu Pro Lys Gly Val Met Leu Thr His
        210                 215                 220

Lys Gly Leu Val Thr Ser Val Ala Gln Gln Val Asp Gly Glu Asn Pro
225                 230                 235                 240

Asn Leu Tyr Phe His Ser Asp Asp Val Ile Leu Cys Val Leu Pro Met
                245                 250                 255

Phe His Ile Tyr Ala Leu Asn Ser Ile Met Leu Cys Gly Leu Arg Val
            260                 265                 270

Gly Ala Ala Ile Leu Ile Met Pro Lys Phe Glu Ile Asn Leu Leu Leu
        275                 280                 285

Glu Leu Ile Gln Arg Cys Lys Val Thr Val Ala Pro Met Val Pro Pro
        290                 295                 300

Ile Val Leu Ala Ile Ala Lys Ser Ser Glu Thr Glu Lys Tyr Asp Leu
305                 310                 315                 320

Ser Ser Ile Arg Val Val Lys Ser Gly Ala Ala Pro Leu Gly Lys Glu
                325                 330                 335

Leu Glu Asp Ala Val Asn Ala Lys Phe Pro Asn Ala Lys Leu Gly Gln
            340                 345                 350

Gly Tyr Gly Met Thr Glu Ala Gly Pro Val Leu Ala Met Ser Leu Gly
        355                 360                 365

Phe Ala Lys Glu Pro Phe Pro Val Lys Ser Gly Ala Cys Gly Thr Val
370                 375                 380

Val Arg Asn Ala Glu Met Lys Ile Val Asp Pro Asp Thr Gly Asp Ser
385                 390                 395                 400

Leu Ser Arg Asn Gln Pro Gly Glu Ile Cys Ile Arg Gly His Gln Ile
                405                 410                 415

Met Lys Gly Tyr Leu Asn Asn Pro Ala Ala Thr Ala Glu Thr Ile Asp
            420                 425                 430

Lys Asp Gly Trp Leu His Thr Gly Asp Ile Gly Leu Ile Asp Asp Asp
        435                 440                 445

Asp Glu Leu Phe Ile Val Asp Arg Leu Lys Glu Leu Ile Lys Tyr Lys
450                 455                 460

Gly Phe Gln Val Ala Pro Ala Glu Leu Glu Ala Leu Leu Ile Gly His
465                 470                 475                 480

Pro Asp Ile Thr Asp Val Ala Val Val Ala Met Lys Glu Glu Ala Ala
                485                 490                 495

Gly Glu Val Pro Val Ala Phe Val Val Lys Ser Lys Asp Ser Glu Leu
            500                 505                 510

Ser Glu Asp Asp Val Lys Gln Phe Val Ser Lys Gln Val Val Phe Tyr
        515                 520                 525
```

-continued

```
Lys Arg Ile Asn Lys Val Phe Phe Thr Glu Ser Ile Pro Lys Ala Pro
            530                 535                 540

Ser Gly Lys Ile Leu Arg Lys Asp Leu Arg Ala Lys Leu Ala Asn Gly
545                 550                 555                 560

Leu

<210> SEQ ID NO 20
<211> LENGTH: 384
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<223> OTHER INFORMATION: "R. palmatum BAS"

<400> SEQUENCE: 20

Met Ala Thr Glu Glu Met Lys Lys Leu Ala Thr Val Met Ala Ile Gly
1               5                   10                  15

Thr Ala Asn Pro Pro Asn Cys Tyr Tyr Gln Ala Asp Phe Pro Asp Phe
            20                  25                  30

Tyr Phe Arg Val Thr Asn Ser Asp His Leu Ile Asn Leu Lys Gln Lys
        35                  40                  45

Phe Lys Arg Leu Cys Glu Asn Ser Arg Ile Glu Lys Arg Tyr Leu His
    50                  55                  60

Val Thr Glu Glu Ile Leu Lys Glu Asn Pro Asn Ile Ala Ala Tyr Glu
65                  70                  75                  80

Ala Thr Ser Leu Asn Val Arg His Lys Met Gln Val Lys Gly Val Ala
                85                  90                  95

Glu Leu Gly Lys Glu Ala Ala Leu Lys Ala Ile Lys Glu Trp Gly Gln
            100                 105                 110

Pro Lys Ser Lys Ile Thr His Leu Ile Val Cys Cys Leu Ala Gly Val
        115                 120                 125

Asp Met Pro Gly Ala Asp Tyr Gln Leu Thr Lys Leu Leu Asp Leu Asp
    130                 135                 140

Pro Ser Val Lys Arg Phe Met Phe Tyr His Leu Gly Cys Tyr Ala Gly
145                 150                 155                 160

Gly Thr Val Leu Arg Leu Ala Lys Asp Ile Ala Glu Asn Asn Lys Gly
                165                 170                 175

Ala Arg Val Leu Ile Val Cys Ser Glu Met Thr Thr Thr Cys Phe Arg
            180                 185                 190

Gly Pro Ser Glu Thr His Leu Asp Ser Met Ile Gly Gln Ala Ile Leu
        195                 200                 205

Gly Asp Gly Ala Ala Ala Val Ile Val Gly Ala Asp Pro Asp Leu Thr
    210                 215                 220

Val Glu Arg Pro Ile Phe Glu Leu Val Ser Thr Ala Gln Thr Ile Val
225                 230                 235                 240

Pro Glu Ser His Gly Ala Ile Glu Gly His Leu Leu Glu Ser Gly Leu
                245                 250                 255

Ser Phe His Leu Tyr Lys Thr Val Pro Thr Leu Ile Ser Asn Asn Ile
            260                 265                 270

Lys Thr Cys Leu Ser Asp Ala Phe Thr Pro Leu Asn Ile Ser Asp Trp
        275                 280                 285

Asn Ser Leu Phe Trp Ile Ala His Pro Gly Gly Pro Ala Ile Leu Asp
    290                 295                 300

Gln Val Thr Ala Lys Val Gly Leu Glu Lys Glu Lys Leu Lys Val Thr
```

```
            305                 310                 315                 320
Arg Gln Val Leu Lys Asp Tyr Gly Asn Met Ser Ser Ala Thr Val Phe
                    325                 330                 335

Phe Ile Met Asp Glu Met Arg Lys Lys Ser Leu Glu Asn Gly Gln Ala
                    340                 345                 350

Thr Thr Gly Glu Gly Leu Glu Trp Gly Val Leu Phe Gly Phe Gly Pro
                    355                 360                 365

Gly Ile Thr Val Glu Thr Val Val Leu Arg Ser Val Pro Val Ile Ser
                    370                 375                 380

<210> SEQ ID NO 21
<211> LENGTH: 348
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<223> OTHER INFORMATION: "R. idaeus BAR"

<400> SEQUENCE: 21

Met Ala Ser Gly Gly Glu Met Gln Val Ser Asn Lys Gln Val Ile Phe
1               5                   10                  15

Arg Asp Tyr Val Thr Gly Phe Pro Lys Glu Ser Asp Met Glu Leu Thr
                    20                  25                  30

Thr Arg Ser Ile Thr Leu Lys Leu Pro Gln Gly Ser Thr Gly Leu Leu
                    35                  40                  45

Leu Lys Asn Leu Tyr Leu Ser Cys Asp Pro Tyr Met Arg Ala Arg Met
50                  55                  60

Thr Asn His His Arg Leu Ser Tyr Val Asp Ser Phe Lys Pro Gly Ser
65                  70                  75                  80

Pro Ile Ile Gly Tyr Gly Val Ala Arg Val Leu Glu Ser Gly Asn Pro
                    85                  90                  95

Lys Phe Asn Pro Gly Asp Leu Val Trp Gly Phe Thr Gly Trp Glu Glu
                    100                 105                 110

Tyr Ser Val Ile Thr Ala Thr Glu Ser Leu Phe Lys Ile His Asn Thr
                    115                 120                 125

Asp Val Pro Leu Ser Tyr Tyr Thr Gly Leu Leu Gly Met Pro Gly Met
                    130                 135                 140

Thr Ala Tyr Ala Gly Phe Tyr Glu Ile Cys Ser Pro Lys Lys Gly Glu
145                 150                 155                 160

Thr Val Tyr Val Ser Ala Ala Ser Gly Ala Val Gly Gln Leu Val Gly
                    165                 170                 175

Gln Phe Ala Lys Leu Thr Gly Cys Tyr Val Val Gly Ser Ala Gly Ser
                    180                 185                 190

Lys Glu Lys Val Asp Leu Leu Lys Asn Lys Phe Gly Phe Asp Glu Ala
                    195                 200                 205

Phe Asn Tyr Lys Glu Glu Ala Asp Leu Asp Ala Ala Leu Arg Arg Tyr
                    210                 215                 220

Phe Pro Asp Gly Ile Asp Ile Tyr Phe Glu Asn Val Gly Gly Lys Met
225                 230                 235                 240

Leu Asp Ala Val Leu Pro Asn Met Arg Pro Lys Gly Arg Ile Ala Val
                    245                 250                 255

Cys Gly Met Ile Ser Gln Tyr Asn Leu Glu Gln Pro Glu Gly Val Arg
                    260                 265                 270

Asn Leu Met Ala Leu Ile Val Lys Gln Val Arg Met Glu Gly Phe Met
```

```
                    275                 280                 285
Val Phe Ser Tyr Tyr His Leu Tyr Gly Lys Phe Leu Glu Thr Val Leu
            290                 295                 300

Pro Tyr Ile Lys Gln Gly Lys Ile Thr Tyr Val Glu Asp Val Val Asp
305                 310                 315                 320

Gly Leu Asp Asn Ala Pro Ala Ala Leu Ile Gly Leu Tyr Ser Gly Arg
                325                 330                 335

Asn Val Gly Lys Gln Val Val Val Val Ser Arg Glu
            340                 345
```

<210> SEQ ID NO 22
<211> LENGTH: 331
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "pTEF1short  version courte du promoteur de
    TEF1 de A. gossypii"

<400> SEQUENCE: 22

```
ccagaatacc ctccttgaca gtcttgacgt gcgcagctca ggggcatgat gtgactgtcg     60
cccgtacatt tagcccatac atccccatgt ataatcattt gcatccatac attttgatgg    120
ccgcacggcg cgaagcaaaa attacggctc ctcgctgcag acctgcgagc agggaaacgc    180 tccccctcaca gacgcgttga attgtcccca cgccgcgccc ctgtagagaa atataaaagg    240
ttaggatttg ccactgaggt tcttctttca tatacttcct tttaaaatct tgctaggata    300
cagttctcac atcacatccg aacataaaca a                                  331
```

<210> SEQ ID NO 23
<211> LENGTH: 1029
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "hph  gne de rsitance  l'hygromycine"

<400> SEQUENCE: 23

```
atgggtaaaa agcctgaact caccgcgacg tctgtcgaga agtttctgat cgaaaagttc     60
gacagcgtct ccgacctgat gcagctctcg gagggcgaag aatctcgtgc tttcagcttc    120
gatgtaggag ggcgtggata tgtcctgcgg gtaaatagct gcgccgatgg tttctacaaa    180
gatcgttatg tttatcggca ctttgcatcg gccgcgctcc cgattccgga agtgcttgac    240
attggggaat tcagcgagag cctgacctat tgcatctccc gccgtgcaca gggtgtcacg    300
ttgcaagacc tgcctgaaac cgaactgccc gctgttctgc agccggtcgc ggaggccatg    360
gatgcgatcg ctgcggccga tcttagccag acgagcgggt tcggcccatt cggaccgcaa    420
ggaatcggtc aatacactac atggcgtgat ttcatatgcg cgattgctga tccccatgtg    480
tatcactggc aaactgtgat ggacgacacc gtcagtgcgt ccgtcgcgca ggctctcgat    540
gagctgatgc tttgggccga ggactgcccc gaagtccggc acctcgtgca cgcggatttc    600
ggctccaaca atgtcctgac ggacaatggc cgcataacag cggtcattga ctggagcgag    660
gcgatgttcg gggattccca atacgaggtc gccaacatct tcttctggag gccgtggttg    720
gcttgtatgg agcagcagac gcgctacttc gagcggaggc atccggagct tgcaggatcg    780
```

```
ccgcggctcc gggcgtatat gctccgcatt ggtcttgacc aactctatca gagcttggtt    840
gacggcaatt tcgatgatgc agcttgggcg cagggtcgat gcgacgcaat cgtccgatcc    900
ggagccggga ctgtcgggcg tacacaaatc gcccgcagaa gcgcggccgt ctggaccgat    960
ggctgtgtag aagtactcgc cgatagtgga aaccgacgcc ccagcactcg tccgagggca   1020
aaggaataa                                                            1029
```

```
<210> SEQ ID NO 24
<211> LENGTH: 236
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "tTEF1  terminateur de TEF1 de A. gossypii"

<400> SEQUENCE: 24
```

```
agtactgaca ataaaaagat tcttgttttc aagaacttgt catttgtata gtttttttat     60
attgtagttg ttctatttta atcaaatgtt agcgtgattt atattttttt tcgcctcgac    120
atcatctgcc cagatgcgaa gttaagtgcg cagaaagtaa tatcatgcgt caatcgtatg    180
tgaatgctgg tcgctatact gctgtcgatt cgatactaac gccgccatcc agtgtc        236
```

```
<210> SEQ ID NO 25
<211> LENGTH: 710
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "pARO10  rgion promotrice de ARO10"

<400> SEQUENCE: 25
```

```
cctatacagg tgtaagactt cttttttgtaa cccacttaat ctcttaggca tgctcttggt     60
attgcgtctc ctcttcttct tgtgtgttta agctacatta tctttgttaa gaataatttg    120
gcgaacccct ttttttcttc ggctttgcaa ggttaattaa catctaccag ttttactaca    180
ttttagattg gttcgtccac cgaaatttaa aaaagcagga ttgaaagcgt acaacaacgt    240
cttagcgaaa aagataatcc aaaattcgat gcttgtacac ctcatgtagc ttccttatta    300
acatttggta gtaggcttag gctatttttt gaaaaagccg tcatatatta ctttgagcct    360
ttgcgaatcc tctccaaagt gtcggttacc taccgggagg ataaccgcg gatagccgtc     420 atttaccgaa aattgccgag gtcatgctga gcatttgtcg tacttttgtg cggcggagct    480
ttgatacctt cggtaagtgt cggtatgtaa taggttagtg gcatcttatt tattgtgttg    540
agtaaagttt aagatataaa ctgggctagt ttgcatcgtc actacagcgg cagctcactt    600
tcattttttt tctgcgttta ttaatactac ataaaatctg atataaaaca tatttaactg    660 atcaacccctc tcaacttgat actcaaaaca agttgacgcg acttctgtaa                710
```

```
<210> SEQ ID NO 26
<211> LENGTH: 703
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "tARO10  rgion terminatrice de ARO10"
```

```
<400> SEQUENCE: 26
aaacttgtgg gcgcaattat aaaacactgc taccaattgt tcgttttctg ttcattaaca        60
cataaaaaac ccttatgtaa ctatatttac aaagtaaata cgtatattat taaagctatt       120
ttaccactac cacagagttc tttgtccagt tgctagtatt ttttttttcg cgacgaggca       180
ggggcgggga gacgtgttgt ttttccacgg ctttcggctc accacttgaa gaactataaa       240
aggccgccaa atttatcctt tttcacttct tccgttcgct tttttctgtc attcctatcg       300
tgtgtttagt agtaggtttt tttgttagaa gaagttttat ccgaaaacta tcgaagacaa       360
atagataaaa aaatctccct cgttctattt gaaactttaa gaaatccata ttaagaaaat       420
acctacatct gctaaatgtc tgctaactta gataaatcct tagacgaaat cattggctct       480
aacaaagcag gaagtaatag agcccgtgtc ggtggtactc gtggtaacgg tccaagaaga       540
gttggtaagc aagttggtag ccaacgtagg agccttccaa acagaagagg ccctatcaga       600
aaaaatacta gggcacctcc aaacgcagtc gctagagttg ccaagctctt ggacaccact       660
agagaggtca aggtcaacgt cgaaggtttg ccaagggaca tta                         703
```